United States Patent [19]
Hogan, Jr. et al.

[11] Patent Number: 5,892,113
[45] Date of Patent: *Apr. 6, 1999

[54] HYDROXYETHYL AMINIMIDES

[75] Inventors: Joseph C. Hogan, Jr., Belmont; David Casebier, Hudson; Paul S. Furth, Medford; Steve Gallion, Woburn; Alan Kaplan, Somerville, all of Mass.

[73] Assignee: Arqule, Inc., Medford, Mass.

[21] Appl. No.: 999,459

[22] Filed: Dec. 29, 1997

Related U.S. Application Data

[62] Division of Ser. No. 326,573, Oct. 20, 1994, Pat. No. 5,734,082.

[51] Int. Cl.$^6$ .................................................. C07C 211/03
[52] U.S. Cl. .............................................................. 564/147
[58] Field of Search .............................. 564/147; 560/32, 560/42, 130, 132, 133

[56] References Cited

U.S. PATENT DOCUMENTS

| | | | |
|---|---|---|---|
| 3,410,880 | 11/1968 | Brockenhurst | 360/404.9 |
| 3,450,673 | 6/1969 | McKillip | 260/75 |
| 3,485,806 | 12/1969 | Bloomquist et al. | 260/80.3 |
| 3,488,327 | 1/1970 | Kollinsky et al. | 260/78.3 |
| 3,488,389 | 1/1970 | McKillip | 260/561 |
| 3,499,032 | 3/1970 | Clemens et al. | 260/561 |
| 3,511,894 | 5/1970 | Markert | 260/875 |
| 3,527,802 | 9/1970 | Slagel | 260/561 |
| 3,555,095 | 1/1971 | Slagel | 260/584 |
| 3,565,868 | 2/1971 | Sedor et al. | 260/78.3 |
| 3,567,725 | 3/1971 | Grabowski et al. | 260/250 |
| 3,583,950 | 6/1971 | Kollinsky et al. | 260/78 |
| 3,598,790 | 8/1971 | Kollinsky et al. | 260/78.3 |
| 3,641,145 | 2/1972 | Culbertson | 260/558 |
| 3,664,990 | 5/1972 | Slagel | 260/85.5 |
| 3,671,473 | 6/1972 | Sedor et al. | 260/18 |
| 3,676,453 | 7/1972 | Pines et al. | 260/307 |
| 3,704,128 | 11/1972 | Koda et al. | 96/50 |
| 3,706,797 | 12/1972 | McKillip et al. | 260/558 |
| 3,706,800 | 12/1972 | Hartlage et al. | 260/561 |
| 3,715,343 | 2/1973 | Slagel et al. | 260/88.1 |
| 3,728,387 | 4/1973 | Freis et al. | 260/561 |
| 3,756,994 | 9/1973 | Culbertson | 260/82.1 |
| 3,781,319 | 12/1973 | Wawzonek et al. | 260/453 |
| 3,794,495 | 2/1974 | Ishihara et al. | 96/87 |
| 3,803,220 | 4/1974 | Gasman | 260/518 |
| 3,811,887 | 5/1974 | Ishihara et al. | 96/50 |
| 3,818,065 | 6/1974 | Schoellkopf et al. | 260/464 |
| 3,828,007 | 8/1974 | Throckmorton | 260/75 |

(List continued on next page.)

FOREIGN PATENT DOCUMENTS

| | | |
|---|---|---|
| 0 185 493 | 6/1986 | European Pat. Off. . |
| 0 212 617 | 4/1987 | European Pat. Off. . |
| 1478953 | 7/1967 | France . |
| 1558886 | 2/1969 | France . |
| 1809950 | 6/1970 | Germany . |
| 63-17933 | 4/1988 | Japan . |
| 1128382 | 9/1968 | United Kingdom . |
| 1 181 218 | 2/1970 | United Kingdom . |
| 1 265 163 | 3/1972 | United Kingdom . |
| 1284304 | 8/1972 | United Kingdom . |
| 93/20935 | 10/1993 | WIPO . |

OTHER PUBLICATIONS

Tetrahedron Letters, 27, 6319 (1986).
Kardiologisisa, "Bioelectrical Mechanism", vol. 31, No. 7, 1991, pp. 52–55.
Kardiologisisa, vol. 30, No. 8, 1990, pp. 69–72.
J. Hetegel Chem., 1972, 9, 687–690, "Aminimides IX(1). A general Synthesis of 1–Substituted–2–imidazolidinones(2)", by David Aelony et al.
J. Org. Chem., vol. 41, No. 4, 1976, 715–716, "Acyl Migration in 2–Hydroxylalkyl Aminimides", by Meir Asscher.
Biopolymers, vol. 17, 1693–1711 (1978), "Experimental Conformational Study of Two Peptides Containing a–Aminoisobutyric Acid. Crystal Structure of N–Acetyl–a–Aminoisobutyric Acid Methylamide" by A. Aubry et al.
Tetrahedron Letters No. 31, pp. 2691–2694, 1976, "Pyridines as Leaving Groups in Synthetic Transformations: Nucleophilic Displacements of Amino Groups, and Novel Preparations of Nitriles and Isocyanates", by J.B. Bapat et al.
University College, Hull, Sep. 27, 1952, pp. 453–456, "The Dehydration and Racemisation on N–Acyl–L–aspartic Acids by Acetic Anhydride", by C.C. Barker.

(List continued on next page.)

Primary Examiner—Brian M. Burn
Attorney, Agent, or Firm—Pennie & Edmond LLP

[57] ABSTRACT

This invention relates to a class of aminimides structurally characterized as an acyl nitrogen-nitrogen ylide such that the acyl moiety possess the structural diversity element G, the quaternary nitrogen possess structural diversity elements E and F, and the quaternary nitrogen is bonded to a hydroxyethyl substituent, which in turn is bonded to an aminomethylene moiety that possess structural diversity elements A and B from the amino group and diversity element c from the methylene substituent, as shown below,

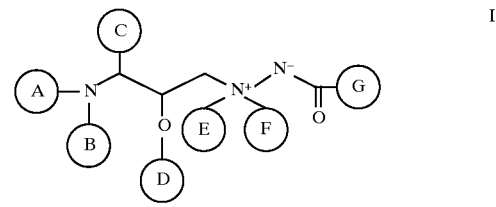

I wherein structural diversity element A, B, C, D, E, F and G are chosen from the set of elements consisting of substituted and unsubstituted as well as branched and straight chain alkyl, aryl, alkaryl, aralkyl, carbocyclic, heterocyclic, hydrogen, amino acid, peptide, polypeptide, protein, depsipeptide, carbohydrate derivatives, nucleotide derivatives, oligonucleotide derivatives, naturally occurring or synthetic organic structural motifs, reporter elements, organic moieties containing at least one polymerizable group, macromolecular component, resin, silicate, other surface and particle support, the diversity elements can be the same, can be different, and can also be connected to form a ringed to several ringed species.

23 Claims, 2 Drawing Sheets

U.S. PATENT DOCUMENTS

| | | | |
|---|---|---|---|
| 3,850,969 | 11/1974 | Grimm et al. | 260/404.5 |
| 3,893,974 | 7/1975 | Niino et al. | 260/47 |
| 3,898,087 | 8/1975 | Brutchen et al. | 96/33 |
| 3,904,749 | 9/1975 | McKillip | 424/71 |
| 3,925,284 | 12/1975 | Carleton et al. | 260/2.5 |
| 3,934,029 | 1/1976 | Kabara | 424/320 |
| 3,934,031 | 1/1976 | Kabara | 424/320 |
| 3,934,035 | 1/1976 | Kabara | 424/320 |
| 3,946,131 | 3/1976 | Biefeld et al. | 428/378 |
| 3,948,866 | 4/1976 | Pennewiss et al. | 260/79.3 |
| 3,963,703 | 6/1976 | Culbertson | 260/239 |
| 3,963,776 | 6/1976 | Middleton | 260/561 |
| 3,968,065 | 7/1976 | Morris et al. | 260/23.5 |
| 3,969,298 | 7/1976 | Gasman | 260/29.6 |
| 3,983,166 | 9/1976 | Samour | 260/481 R |
| 3,985,807 | 10/1976 | Grimm et al. | 260/561 |
| 4,005,055 | 1/1977 | Miron et al. | 260/47 |
| 4,016,340 | 4/1977 | Kolesinski et al. | 526/7 |
| 4,022,623 | 5/1977 | Fitzgerald et al. | 96/114 |
| 4,046,658 | 9/1977 | Brown | 204/181 |
| 4,067,830 | 1/1978 | Kresta | 260/2.5 |
| 4,070,348 | 1/1978 | Kriemer et al. | 260/79.3 |
| 4,078,901 | 3/1978 | Sung et al. | 44/64 |
| 4,080,206 | 3/1978 | Kolesinski et al. | 96/29 |
| 4,097,444 | 6/1978 | Teige et al. | 260/40 |
| 4,102,916 | 7/1978 | Falk | 260/501.12 |
| 4,122,159 | 10/1978 | Madrange et al. | 424/45 |
| 4,140,680 | 2/1979 | Sullivan | 526/287 |
| 4,162,355 | 7/1979 | Tsibris | 526/293 |
| 4,189,481 | 2/1980 | Kabara | 424/248.54 |
| 4,212,905 | 7/1980 | Talbris | 427/221 |
| 4,213,860 | 7/1980 | Tsibris | 210/31 |
| 4,217,364 | 8/1980 | Kabara | 424/320 |
| 4,260,705 | 4/1981 | Tsibris | 525/330 |
| 4,280,008 | 7/1981 | Scheollkopf et al. | 548/301 |
| 4,304,705 | 12/1981 | Heilmann et al. | 260/30.4 |
| 4,378,411 | 3/1983 | Heilmann et al. | 428/500 |
| 4,424,272 | 1/1984 | Taylor | 430/507 |
| 4,451,619 | 5/1984 | Heilmann et al. | 525/379 |
| 4,485,236 | 11/1984 | Rasmussen et al. | 544/69 |
| 4,548,981 | 10/1985 | Kolesinski et al. | 524/555 |
| 4,563,467 | 1/1986 | Soler | 514/336 |
| 4,617,253 | 10/1986 | Taylor et al. | 430/323 |
| 4,624,995 | 11/1986 | Katritzky et al. | 525/452 |
| 4,645,711 | 2/1987 | Winslow | 428/355 |
| 4,667,012 | 5/1987 | Rasmussen et al. | 528/332 |
| 4,670,528 | 6/1987 | Taylor et al. | 526/263 |
| 4,695,608 | 9/1987 | Engler et al. | 525/308 |
| 4,705,824 | 11/1987 | Lin | 524/612 |
| 4,737,560 | 4/1988 | Heilmann et al. | 526/304 |
| 4,740,568 | 4/1988 | Katritzky et al. | 525/452 |
| 4,777,217 | 10/1988 | Rasmussen et al. | 525/279 |
| 4,777,276 | 10/1988 | Rasmussen et al. | 556/419 |
| 4,785,070 | 11/1988 | Rasmussen et al. | 528/73 |
| 4,816,554 | 3/1989 | Katritzksy et al. | 528/210 |
| 4,841,021 | 6/1989 | Katritzky et al. | 528/407 |
| 4,852,969 | 8/1989 | Babirad et al. | 350/96.34 |
| 4,871,824 | 10/1989 | Heilmann et al. | 526/304 |
| 4,874,822 | 10/1989 | Rasmussen et al. | 525/279 |
| 4,898,923 | 2/1990 | Katritzky et al. | 528/73 |
| 4,948,715 | 8/1990 | Hulme-Lowe et al. | 430/495 |
| 4,981,933 | 1/1991 | Fazio et al. | 526/260 |
| 5,013,795 | 5/1991 | Coleman et al. | 525/279 |
| 5,039,813 | 8/1991 | Fazio et al. | 548/228 |
| 5,066,559 | 11/1991 | Elmasry et al. | 430/111 |
| 5,075,352 | 12/1991 | Elmasry | 523/201 |
| 5,081,197 | 1/1992 | Heilmann et al. | 526/260 |
| 5,091,489 | 2/1992 | Heilmann et al. | 526/90 |
| 5,094,766 | 3/1992 | Kepuscinski et al. | 252/51.5 |
| 5,138,071 | 8/1992 | Schoellkopf et al. | 548/537 |
| 5,147,957 | 9/1992 | Kumar | 528/15 |
| 5,149,806 | 9/1992 | Moren et al. | 544/72 |
| 5,157,108 | 10/1992 | Krepski et al. | 528/503 |
| 5,157,145 | 10/1992 | Schoellkopf et al. | 560/41 |
| 5,175,081 | 12/1992 | Krepski et al. | 430/617 |
| 5,185,102 | 2/1993 | Harelstad et al. | 252/582 |
| 5,194,623 | 3/1993 | Krepski et al. | 548/261 |
| 5,200,471 | 4/1993 | Coleman et al. | 525/326.9 |

OTHER PUBLICATIONS

Acta Chem. Scand. B 33 (1979) No. 2, "Electron Deficient Heteroaromatic Ammonioamidates. XVII. N–(3–Quinazolinio)amindates. VI. The Photochemistry of N–(30Quinazolinio)amidates in the Presence of α–Toluenethiol", by G. Barta–Szalai et al.

J. Chem. Socl. Perkin Trans. I 1983, "Electron Deficient Heteroaromatic Ammonioamides. Part 24.[1]. N–(Quinazolin–3–io)amindates. Part 11.[2] The Photochemistry of N–(6,7–Methylenedioxyquinazolin–3–io)amidates in Acetone", by Gizella Barta–Szalai et al.

J. Heterocyclic Chem., 23, 375, 1986, "Novel Synthesis of Pyrido[2,1–f]–as–Triazinium System and its Zwitterionic Derivatives . . . ", by S. Batori.

J. Heterocyclic Chem., 25, 437 (1988), "Regioselectivity in Methylation and Phenylation of the Zwitterionic Pyrido[2,1–f]–as–triazinium–1– and 3–olates and thiolates[1]", by Sandor Batori et al.

J. Heterocyclic Chem., 27, 1673 (1990), "Synthesis and Regiospecificity in Methylation of Pyrido[1,2–a]pyrazinium–1– and 3–olates and Pyrido[1,2–b]pyridazinium–2– and 4–olates [1]", by S. Batori et al.

J.C.S. Perkin II, 1978, 1173, "The Basicities of Substituted N–Trimethylammoniophenylacetamidates and N–Trimethylammoniocinnamamidates. The Hammett Correlations and the Thermodynamics of Protonation", by William H. Beck.

J.C.S. Perkin II, 1976, "The Basicities of N–Trimethylammonioacetamidate and of Substituted N–Trimethylammoniobenzamidates. The Hammett Correlation and the Thermodynamics of Protonation", by William H. Beck et al.

Tetrahedron Letters, No. 4, pp. 289–292, 1972, "The Curtius Rearrangement in Aminimides" by Herman P. Benecke et al.

J. Am. Chem. Soc., 1982, 104, 2437–2444, "Solid–State and Solution Conformation of Homo Oligo–α–aminoisobutyric acids) from Tripeptide to Pentapeptide: Evidence for a 310 Helix[1a]", by Ettore Benedetti.

J. Am. Chem. Soc. 1984, 106, 8146–8152, "Folded and Extended Structures of Homooligopeptides from α,α–Dialkylated Glycines. A Conformational Energy Computation and X–ray Diffraction Study, Ettore Benedetti et al.

Gaza Chem. Ital. 95, 1965, "Reazione dei diarildiazoalcani–Nota IV. Difenildiazometano e azoici carbonilici", Gian Franco Bettinetti et al.

Nucleosides & Nucleotides, 10(8), 1657–1665, 1991 "Synthesis of N–Aminopyrazinium Analogs of Cytidine and 2'–Deoxycytidine", by Miroslav Bobek et al.

J. Am. Chem. Soc. 1984, 106, 8152–8156, "Folded and Extended Structures of Homooligopeptides from α,α–Dialkylated α–Amino Acids. An Infrared Absorption and H Nuclear Magnetic Resonance Study", by Gian Maria Bonora.

Bull. Soc. Chim. Belg., vol. 84/n4/1975, pp. 299–304, "Synthesis of a Homologous Series of Protected Oligopeptides Derived From L–Norvaline" by G.M. Bonora et al.

Tetrahedron vol. 38, No. 24, pp. 3579–3583, 1982, "(–)–Isovaline: Confirmation of its D–(+R)–Configuration by X–Ray Analysis of Its N–Chloroacetyl Derivative", by R. Bosch et al.

Tetrahedron Letters No. 31, pp. 2689–2690, 1976, "Allylic and Benzylic Deamination By Thermal Cleavage of 1–substituted 1,2–Dihydro–2, 4, 6–Triphenylpyridines" by A.J. Boulton et al.

Chemistry and Industry, 11 Jul. 1970, "Kinetics of reaction between gaseous oxygen and cobalt(II) ammines" by R. Bratchley et al.

Tetrahedron Letters vol. 21, 5059–5060, 1980, "New Cyclic Aminimides Containing Pyrazolone Skeleton", By M. Poje and N. Bregant.

Biopolymers, vol. 12, 2599–2605 (1973), "An Obligatory a–Helical Amino Acid Residue" by Antony W. Burgess et al.

J. Chem Soc., 1972, 1071–1076, "Structural Investigations of Ylides. Part I. Crystal and Molecular Structures of Trimethylammoniobenzamidate and Trimethylammonionitramidate: Two Stabilised Nitrogen–Nitrogen Ylides", by A.F. Cameron.

Chemical Communications, No. 14, Jul. 21, 1971, 725–726, "Crystal and Molecular Structures of Two N–Ammonio–a–midates", by A.F. Cameron.

Journal of Pharmaceutical Sciences, vol. 75, No. 4, Apr. 1986, 407–409, "2,2'–Phthaloyl–, 2,2'–Isophthaloyl–, and 2,2'–Terephthaloylbis[1,1,1–trimethylhydrazinium] Dihydroxie, Bis(Inner Salts): Synthesis, Partition Coefficients, Toxicity and Effect on Ganglionic Transmission", Lindley A. Cates.

Chemical Abstracts, vol. 89, 1978, p. 250, Mosquito larvicidal and pupicidal activity of aminimides", by E. Clarke et al.

"Synthesis of 2,2'–Bis–[5(4H)–oxazolones]" by S. Charles Cleaver et al, 1954, vol. 77, pp. 1544–1546.

Meth and Find Exptl Clin Pharmacol 1987; 9(2):101–110, "Pharmacological Properties of Besulpamide, a New Diuretic, in Rats and Dogs", by M. Colombo, et al.

Biochemical and Biophysical Research Communications, vol. 79, No. 1, 1977, "The Crystal and Molecular Structure of the Amino Terminal Tetrapeptide of Alamethicin. A Novel $3_{10}$ Helical Conformation.

Newcastle Technical Centre, 1274–1280, Jun. 1969, "Light Scattering by Polydisperse Cylindrical Micelles", by J.M. Corkill et al.

Tetrahedron, vol. 49, No. 15, pp. 3185–3192, 1993, "2–Alkoxycarbonylcycloimmonium Ylides, Efficient 1,4–Dipole Equivalents in the Synthesis of New Conjugated Betaines", by Ana M. Cuadro et al.

Journal of Polymer Science, Part A–1, vol. 6, 363–373 (1968), "Aminimides. IV. Homo– and Copolymerization Studies on Trimethylamine Methacrylimide", by B.M. Culbertson.

Macromolecules, vol. 1, p. 254, May–Jun. 1968, "Aminimides. VII. Homo– and Copolymerization Studies on 1,1–Dimethyl–1–(2–hyroxypropyl)amine–Methacrylimide . . . ", by B.M. Culbertson.

Aminimides, vol. 3, No. 6, Nov.–Dec. 1970, 715–722, "Aminimides. VIII Synthesis and Homo–and Copolymerization Studies of 1,11–Trimethylactrylylhydrazinium Chloride and 1,1,1–Trimethylmethacrylylhydrazinium Chloride", by B.M. Culbertson et al.

Journal of Polymer Science: Part A–1, vol. 6, 2197–2207 (1968), "Aminimides V. Preparation and Polymerization Studies of Trimethylamine–4–Vinylbenzimide", by B.M. Culbertson et al.

Applied Polymer Symposium No. 26, 399–410 1975, "Synthesis and Polymerization Studies of Aminimide Monomers Containing Acetoxyl or Carboxylic Acid Residues", by B.M. Culbertson et al.

J. Org. Chem, USSR 1966, 2, Aminimides cyclic.

Meth and Find Exptl Clin Pharmacol 1987; 9(2):111–119, "Acute, Subacute and Subchronic Toxicity of Besulpamide", by I. Demestre et al.

Tetrahedron vol. 48, No. 23, pp. 4733–4748, 1992, "Asymmetric Synthesis of Unusual Amino Acids: An Efficient Synthesis of Optically Pure Isomers of β–Methylphenylalanine" by Ramalinga Dharanipragada et al.

Inorg. Nucl. Chem. Letters, vol. 10, pp. 233–235, 1974, "Ortho–Metallation Reactions With 1–Benzoyliminopyridinium Betaine", by Shelton A. Dias et al.

J. Chem Soc., 162, 1975, J.C.S. Dalton, "Metal–Ylide Complexes. Part I. Metallation Reactions . . . ", by Shelton A. Dias et al.

Chemical Abstracts, vol. 70, 1969, 264, "Synthesis of 1–alkyl–1,1–dimethylhydrazinium salts and N–alkyldimethylaminoacetimides and their properties", Kameyama, Eiichi et al.

Meth and Find Exptl Clin Pharmacol 1987; 9(2):121–126, "Pharmacokinetics of Besulpamide in Rats and Dogs", by J. Esteve.

Chemical Abstracts, vol. 115, 1991, p. 44, "Elimination of disturbances of the heart electric stability and arrhythmias with a synthetic analog of acetylcholine" by F.Meerson et al.

Polymer Bulletin 22, 449–454(1989), "Synthesis and reactivity of highly versatile VDMO–VBC copolymers" by Robert C. Fazio et al.

Tetrahedron, vol. 31, pp. 2559–2569, 1975, "N–(6, 7–Methylenedioxy–3–Quinazolinio)Amidates–I Synthesis Spectra and Some Dark Reactions", J. Fetter.

J. Chem. Soc. Perkin Trans. II 1982, pp. 1235–1239, "The Crystal Structure of the Amino–terminal Pentapeptide of Suzukacillin. Occurrence of a Four–fold Peptide Helix", by Athappilly K. Francis.

Biopolymers, vol. 22, 1499–1505 (1983), "Crystal Structure of Boc–Ala–Aib–Ala–Aib–Aib–Methyl Ester, A Pentapeptide Fragment of the channel–Forming Inonophore Suzukacillin", by A.K. Francis et al.

J. Chem. Research (S), 192–193, 1988, "Photochemistry of Trialkylammonio–N–benzoylimides: Rearrangement and Amide Formation" by Sally Freeman et al.

J. Chem. Research(S), 354–355 1989, "Base–induced Rearrangement of 1,1,1,2–Tetraethyl–2–benzoylhydrazinium Iodide to N–(Dimethylaminomethyl)–N–methylbenzamide" by Sally Freeman et al.

J. Heterocyclic Chem., 26, (Sep.–Oct. 1989), 1373–1382, Study of the Structure of Besulpamide, 1–[–Chloro–3–sulfamoylbenzoyl)amino]2,4,6–trimethylpyridinium hydroxide inner salt, and related compounds, using X–ray Crystallography and 'H and $^{13}$C Nuclear Magnetic Resonance Spectroscopy", Jordi Frigola et al.

Chemical Communications, 1968, 917–918, "The Crystal Structure of a Novel Heterocycle containing an Intramolecular Carbon–Nitrogen Hydrogen Bond", by Charles J. Fritchie et al.

J.C.S. Perkins II, 1978, 431, "Basicity of the Carbonyl Group. Part 6, Calorimetric and Spectometric Study of Complexation of para–substituted N–Ammoniobenz–amidates by Boron Trifluoride", by Jean–Francois Gal et al.

Intra–Science Chemistry Reports, vol. 5, No. 4, 1971, pp. 305–316 "Studies on the Biologically–Active Conformations of Angiotensin" by Garland.

J. Chem. Soc. (C), 1967, 2577–2580, Thermolysis of Trimethylamine–benzimide and Related Compounds: Identification of By–products and their Probable Mechanism of Formation" by Martin S. Gibson et al.

Acta Chem. Scand. 9 (1955), No. 9, 1498–1509, "The Reaction of Hydrazine with Cinnamic Acid Derivatives", by W.O. Godtfredsen et al.

Polymer Letters, vol. 2, pp. 1095–1096 (1964), "Thermally Reversible Homopolymer Gel Systems", by Howard Haas et al.

Tetrahedron Letters, No. 26, pp. 1733–1737, 1964, "Beaktionen von Benzol–Derivaten Mit Nitrenen", by Klaus Hafner et al.

Lipids, vol. 20, No. 10 (1985), 685–692, "Hypolipidemic Activity of the Surfactants Aminimides, and Their Effects on Lipid Metabolism of Rodents", by Iris H. Hall.

Int. J. Peptide Protein Res. 21, 1983, 392–405, "Peptides containing dipropylglycine", by Paul M. Hardy et al.

Bull. Soc. Chim. Belg., 65, pp. 291–296, 1956, "Syntheses des isocyanates de vi2nyle et d'isoprpenyle", by R. Hart.

Journal of Fluorine Chemistry, 51, 1991 419–431, "Amine-(polyfluoroalkoxyacyl)imide Surfactants[1]", by Lisa Haywood et al.

Journal of Polymer Science, vol. 22, 3149–3160(1984), "Chemistry of Alkenyl Azlactones. IV. Preparation and Properties of Telechelic Acrylamides Derived from Amine–terminated Oligomers" by Steven M. Heilmann et al.

J. Am. Chem. So., 1982, 104, pp. 2437–2444, "Solid–State and Solution Conformation of Homo Oligo (α–aminoisobutyric acids) from Tripeptide to Pentapeptide: Evidence for a $3_{10}$ Helix$^{1a}$.

J. Med. Chem. 1991, 34, 1777–1789, "Synthesis, Conformational Properties, and Antibody Recognition of Peptides Containing β–Turn Mimetics Based on α–Alkylproline Derivatives" by Mark G. Hinds.

J. Org. Chem., 24, 1825, vol. 28 (1959), "Alkyl–(alkoxyalkyl–)hydrazones", by John C. Howard et al.

Biopolymers, vol. 22, 517–530(1983), "Conformational and Dynamic Considerations in the Design of Peptide Hormone Analogs", by Victor J. Hruby et al.

Die Angewandte Makromolekulare Chemie 11 (1970) 109–124, "Syntheses und Reaktionen von 2–Alkenyloxazolonen" by Von Klaus Hubner et al.

Liebigs Ann. Chem. 1977, 506–527, "Additionen mit Chinolinium–, Isochinolinium– und Phenanthridinium–N–imid", by Rolf Huisgen et al.

Journal of the American Oil Chemists' Society, vol. 55, Feb. 1978, "Properties of 2–Hydroxyethylamine Acylimide Aqueous Solution—Unusual Clouding Phenomenon", Isao Ikeda et al.

Journal of the American Oil Chemists' Society, vol. 53, 1976, "Synthesis of 1,1,1–Tris(2–hyrdoxyethyl)amine–2–acylimide", Isao Ikeda et al.

Organic Mass Spectrometry, 1971, vol. 5, pp. 61 to 71, "The Mass Spectra of N–Acyliminopyridinium and Isoquinolinium Betaines", by M. Ikeda et al.

The Chemical Society of Japan, No. 3, 1982, "Synthesis, Surfactant Properties and Catalytic Action of Crown Ethers Bearing Aminimide Group", by Seiichi Inokuma et al.

Journal of Polymer Science: Part A: Polymer Chemistry, vol. 25, 1363–1382 1987, "Thermal Decomposition Behavior of Bis–aminimides and Their Application to Polymerization of Epoxide" by Shinzo Inubushi et al.

Journal of Polymer Science: Part A: Polymer Chemistry, vol. 25, 137–150 (1987), "Thermal Decomposition Behavior of Mono–aminimides and Their Application to Polymerization of Epoxide", by Shinzo Inubushi et al.

Journal of Polymer Science, Part A:, Polymer Chemistry, vol. 26, 1779–1789 (1988), "Tough Epoxy Resins Cured with Aminimides", by Shinzo Inubushi et al.

Can. J. Chem., vol. 52, 1974, 3671–3675, "New Route to Cyclic Azomethine Imines", By P.C. Ip et al.

The Journal of Organic Chemistry, Aug. 31, 1966, "Synthesis of N–[1–(1–Substituted 2–oxopropyl)]acrylamides and –methacrylamides. Isolation and some Reactions of Intermediates of the Dakin–West Reaction", by Yosmo Iwakura et al.

Journal of Molecular Structure, 243 (1991) 365–368, "A Multinuclear NMR Study On Some Cyclic Aminimides and Related Compounds", by J. Jazwinski.

Biopolymers, vol. 22, 241–246(1983), "Stabilizing Effects of 2–Methylalaline Residues on β–Turns and α–Helixes", by G. Jung.

Coyright 1981 by Walter de Gruyter Berlin, Structure and Activity of Natural Peptides, "Properties of the Membrane Modifying Polypeptide Antibiotics Alamethicin and Trichotoxin A–40, by Gunther Jung.

Journal of the American Oil Chemists' Society, 52, 1975, "Aminimides: II. Antimicrobial Effect of Short Chain Fatty Acid Derivatives", by J.J. Kabara et al.

Chemistry Letters, pp. 413–414, 1976, "Synthesis and Characterization of 1–Imidoyliminopyridinium N–Ylides", by Akikazu Kakehi et al.

Chemical Abstracts, vol. 72, 1970, 45292–45293, "Reactive surfactants. II. Synthesis of 2–acyl–1,1,1–trimethylhydrazinium hydroxide inner salts and their properties", by E. Kameyama et al.

Nippon 1974, No. 9, 1789, "Preparation and Some Properties of (2–Hydroxyalkyl)–dimethylammonium–N–acylimine", by Eiichi Kameyama et al.

Chem. Phar. Bull., vol. 23, 1975, 452–455, "Studies on Ketene and Its Derivatives. LXVIII Reaction of Kiketene with N–Imino–pyridinium, –quinolinium, and –isoquinolium Ylides", Tetsuzo Kato et al.

Gazzetta Chimica Italiana, 117, 1987, 509–511, "The Structure of the Pyridine 1–Benzimide Mono Cation", by Alan R. Katritzky.

J.C.S. Perkin I, 1979, "Heterocycles in Organic Synthesis. Part 17. Conversion of Primary Amines into Bromides and Chlorides", by Alan R. Katritzky et al.

J.C.S. Perkin I, 1979, "Heterocycles in Organic Synthesis. Part 19, Thermolysis of Pyridinium N–Acylimines: a New Preparation of Isocyanates", by Alan R. Katritzky et al.

J.C.S. Perkin I, 1979, "Heterocycles in Organic Synthesis, Part 16, The Conversion of Aliphatic, Aromatic, and Heteroaromatic Primary Amines into Iodides" by Alan R. Katritzky et al.

J.C.S. Perkin I, 1979, "Heterocycles in Organic Synthesis. Part 24. A New Synthesis of NN'–Diarylcarbodi–imides", by Alan R. Katritzky et al.

Angew: Chem. Int. Ed. Engl. 23 420–429, 1984, Pyrylium Mediated Transformations of Primary Amino Groups into Other Functional Groups, by Alan R. Katritzky et al.

J.C.S. Perkin I, 1981, 1495–1500, "Reactions of Pyryliums with Mono–and asym–Di–substituted Hydrazines" by Alan R. Katritzky et al.

Heterocycles, vol. 18, 1982, "Pyrazolo(1,5–c)Pyrimidines from pyrylium Salts and Amidrazones and Pyridine Imidoyl–N–Imides from Imidoyl Chlorides", by Alan R. Katritzky et al.

J. Am. Chem. Soc. 1991, 113, 2275–2283, "Topographic Design of Peptide Neurotransmitters and Hormones on Stable Backbone Templates: Relation of conformation and Dynamics to Bioactivity" by Wieslaw M. Kazmierski et al.

J. Org. Chem., 1981, 46, 2490–2497, Relative Reactivity and Structures of Benzoyltrimethylhydrazine and 1–Benzoyl–2–methylpyrazolidine", by Spencer Knapp.

Journal of Polymer Science: Polymer Chemistry Edition, vol. 21, 3597–3600 1983, "Synthesis of Polymers Containing Pyridinium Ylide and Iminopyridinium Ylide Structure", by S. Kondo et al.

Chem. Berg. 103, 2052–2061 (1970), Umlagerung von quartaren Allyl–, Benzyl– und Propargyl–hydraziniumsalzen, by Karl–Heinz Konig et al.

Tetrahedron, vol. 38, No. 14, pp. 2165–2181, 1982, "Syntheses von 2–Methylalanin–Peptiden, die pH–Abhangigkeit Ihrer $^{13}$C–NMR–Spektren und Eine Neue Methode Zur Auswertung uber CS–Diagramme," by Dieter Liebfritz.

Chemica Scripta. 1978–79, 13, 195–196, "Electron Deficient Heteroaromatic Ammonioamidates, $20^1$; N–(3–Quinazolinio)amidates, $8^1$", by M. Lempert–Sreter, et al.

J. Chem. Soc. Perkin Trans. 1 1983, "Electron Deficient Heteroaromatic Ammonioamides., etc.", by Magda Lempert–Sreter et al.

Tetrahedron, 1960, vol. 11, pp. 39 to 51., "Synthesis of Peptides Derived From Alpha–Methylalanine", by M.T. Leplawy et al.

Helvetica Chimica Acta – vol. 65, Fasc. 1 (1982)–Nr. 18, "18. Azimine. VI. $^{12}$) 1–Alkoxycarbonyl–2,3–dialkyl– und – 2,3–diaryl–azimine" by von Christian Leuenberger.

Monatshefte fur Chemie, 120, 749–758 (1989), "1–Amino–2–hydrazinopyrimidin–N–ylides. Unusual Tautomers of 1–Aminopyrimidin–2–hydrazones", by Jurgen Liebscher.

J.C.S. Perkin, Trans 2, 1977, 909–914, "Mono– and Di–protonation Sites in N–Ammonio–amidates: a Specro–scopic Study", by Milica Liler.

J.C.S. Perkins II, 1980, 380, "The Kinetics of Hydrolysis of N–Trimethylammonioacetamide and of Substituted N–Trimethylammoniobenzamides in Concentrated Sulphuric Acid", by Milica Liler et al.

J.C.S. Chem. Comm., 1975, 93–94, "Methylation and Protonation Sites in Some N–Ammonioamidates" by Milica Liler et al.

Tetrahedron Letters No. 30, 2621–2624, 1974, "A convenient Thermal Route to N,N–Dialkylaminoisocyanates", by William J.S. Lockley.

Tetrahedron Letters No. 48, 4263–4266, 1974, "Cyclic Aminimides Containing The pyrazolone Skeleton", by William J.S. Lockley.

Canadian Journal of Chemistry, vol. 50, 1972, "Reaction of Diphenylcyclopropenethione with Pyridinium Imines", by J.W. Lown et al.

Tetrahedron Letters No. 5., 425–428, 1971, "Cycloadditions of Aminoisocyanates to Heterocumulenes", by Walter Lwowski et al.

Supplement II to Circulation Research, vols. XXX and XXXI, Sep. 1972, pp. 143–150, "Angiotensin II—Studies on the Biologically Active Conformation", by Garland R. Marshall, et al.

Plastics Manufacturing., vol. 83, 1975, "Amine imides" by Kanji Matsueda et al.

Liebigs Ann. Chem. 1980 715–724, "Die Kristallstruktur von α(tert–Butyloxycarbonylamino)–isobuttersaure" by Wilfried Mayr et al.

Canadian Journal of Chemistry, vol. 45, 1967, Aminimides. I. "A General Synthesis of Aminimides From Acyl Hydrazides and Their Pyrolysis", by William J. McKillip.

Canadian Journal of Chemistry, vol. 45, 1967, 2619–2622, "Aminimides. II. A one–step synthesis of aminimides from carboxylic acid esters", by William J. McKillip.

Chemical Reviews, 1973, vol. 73, No. 3, pp. 255–281, "The Chemistry of Aminimides", by W.J. McKillip et al.

Chemical Abstracts, vol. 114, 1991, p. 40, "Antiarrhythmic effect of adaptive activation of the vagal system and a new synthetic acetylcholine analog", by F.Z. Meerson.

Journal of Polymer Science: Polymer Chemistry Edition, vol. 21: 1159–1164 1983, Synthesis of Aminimide Monomers and Polymers, Avinash C. Mehta et al.

Journal of Polymer Science: Part A: Polymer Chemistry, vol. 29, 29–37(1991), "Copolymers of 2–Vinyl–4,4–Dimethylazlactone with Styrene and Ethyl α–Hydroxymethylacrylate" by Jeno Muthiah et al.

Ace. Chem. Res. 1981, 14, pp. 356–362, "Alamethicin, a Transmembrane Channel" by Ramakrishnan Nagaraj et al.

Acc. Chem. Res. 1981, 14, 356–362, "Alamethicin, a Transmembrane Channel", Ramakrishnan Nagaraj et al.

Journal of the American Chemical Society, 101:1, Jan. 3, 1979, "Stereochemically Constrained Linear Peptides. Conformations of Peptides Containing α–Aminoisobutyric Acid", by R. Nagaraj et al.

Acta Cryst. (1980), B36, 1498–1500, "Structure of a Peptide Oxazolone: 2–(1'–Benzyloxycarbonylamino–1'–methylethyl)–4, 4–dimethyl–5–oxazolone", by C.M.K. Nair et al.

Tetrahedron Letters, vol. 30, No. 49, pp. 6845–6848, 1989, "Asymmetric Synthesis of Unusual Amino Acids: Synthesis of Optically Pure Isomers of α–methyltyrosine", by Ernesto Nicolas.

Journal of Applied Polymer Science, vol. 27, 2361–2368 1982, "Aminimide as Hardener/Curing Promoter for One Part Epoxy Resin Composition", by Hideki Niino et al.

Chem Pharm Bull, vol. 11 (1963), pp. 774–748, "Pyridazine Derivatives IV. The Structures of Aminopyridazines", by Yoshiro Nitta.

Journal of Applied Polymer Science, vol. 27, 2361–2368 (1982), "Aminimide as Hardener/Cruing Promotor for One Part Epoxy Resin Composition", by Hideri Nhno and Saburo Noguchi.

Chem. Pharm. Bull., vol. 14(5) 518–523, 1966, "Reaction of N–Aminopyridinium Derivatives.V. Syntheses of 1–(N–Methylacetamido)alkylpyridinium Salts and Their Reaction with Cyanide Ion", by Toshihiko Okamoto et al.

Tetrahedron, vol. 41, No. 12, 2239–2329, 1985, "Heterocyclic Mesomeric Betaines", by W. David Ollis.

J. Am. Chem. Soc., vol. 103, No. 11, 1981, pp. 2948–2955, "Sensitivity of Polypeptide Conformation to Geometry. Theoretical Conformational Analysis of Oligomers of – Aminoisobutyric Acid", by Yvonne Paterson et al.

J. Org. Chem., 1982, 47, 5023–5025, Degradation of Aminimides Obtained from Enamines and (Ehoxycarbonyl)nitrene", by Lucio Pellacani et al.

Journal of Molecular Structure, 86 (1982) 341–347, "Quantum Theory of the Structure and Bonding in Proteins", by David Peters and Jane Peters.

J.C.S. Dalton I, 1978, 1155, "Reactions of 2–Azidopyridine and 1–Pyridinio Ylides with Transition–metal Complexes", by Maddalena Pizzotti.

The Journal of Organic Chemistry, vol. 33, No. 10, Oct. 1968, "Bridgehead Nitrogen Heterocycles. I. A Convenient Synthesis of Pyrazolo[1,5–a]pyridines", by K.T. Potts et al.

J. Chem. Soc., Perkin Trans. 1 1983, 417–421, "Molecular Structure of Boc–Aib–Aib–Phe–Met–NH$_2$ DMSO. A Fragment of a Biologically Active Enkephalin Analogue", by B.V. Venkataram Prasad, et al.

Tetrahedron Letters No. 37, 3249–3252, 1974, "Cyclic Aminimides Containing the 3–oxo–5–Thioxo–1,2,4–Triazolidine Skeleton: Rearrangements of 5–Thiourazole Derivatives", by V.T. Ramakrishnan.

Biochemical and Biophysical Research Communications, vol. 103, No. 3, 1981, pp. 898–904, "Hydrophobic Channels in Crystals of an x–Aminoisobutyric Acid Pentapeptide", by Ch. Pulla Rao et al.

Biopolymers, vol. 21, 2461–2472 (1982), "Molecular Structure of t–Butyloxycarbonyl–Leu–Aib–Pro–Val–Aib–Methyl Ester, a Fragment of Alamethicin and Suzukacillin: a $3_{10}$–Helical Pentapeptide", by Ch. Pulla Rao et al.

Makromol. Chem., Rapid Commun. 5,67–70 (1984), "Chemistry of Alkenylazlactones, $2^{a)}$ Reaction with thiols", by Jerald K. Rasmussen et al.

J. Heterocyclic Chem., 27, 1041 (1990), "Synthesis of Some N–[Pyridyl(phenyl)carbonylamino]–alkyl–1,2,3,6–tetrahydropyridines", by Kinfe K. Redda.

J. Med. Chem., 1979, vol. 22, No. 9, 1079, "Syntheses of N–Substituted 2,(3,4)–Pyridylcarboxylic Acid Hydrazides with Analgesic and Antiinflammatory Activity", by Kinfe Redda et al.

Journal of Pharmaceutical Sciences, vol. 81, No. 5, May 1992, "Synthesis and Pharmacological Evaluation of Some N–[Pyridyl(phenyl)carbonylamino]methyl–1,2,3,6–tetrahydropyridines" by Kinfe K. Redda et al.

Chem. Pharm. Bull. 39 (3) 786–791 1991, "Synthesis and Anti–inflammatory Activities of Some N–[Pyridyl(penyl)carbonylamino]–tert–butyl/phenyl–1,2,3,6–tetrahydropyridines" by Kinke K. Redda et al.

Nature, vol. 300, Nov. 1982, pp. 325–330, Articles—"A voltage–gated ion channel model inferred from the crystal structure of alamethicin at 1.5–A resolution", by Robert O. Fox, Jr. & Frederic M. Richards.

Tetrahedron, vol. 49, No. 18, pp. 3767–3780, 1993, "Electrophilic Amination of Pyrimidine–2–thiones—Synthesis of Zwitterionic 2–Aminothiopyrimidinium–N–ylides, Pyrimidine–2–ones and Bicyclic Pyrimidinium Compounds", by Beate Riemer et al.

Acta Cryst. (1983), C39, 894–896, "tert–Butyl oxycarbonyl–α–aminoisobutyryl–α–aminoisobutyrate Benzyl Ester, $C_{20}H_{30}N_2O_5$", by Patrick Van Roey et al.

Int. J. Peptide Protein Res. 19, 1982, 499–505, "Crystal and molecular structure of tert.–butyloxycarbonyl–L–hydroxyprolyl–α–aminoisobutyryl–α–aminoisobutryl–L–phenylalaninol" by Patrick Van Roey et al.

Biopolymers, vol. 32, 407–410 (1992), "Peptidomimetics as Receptors Agonists or Peptidase Inhibitors: A Structural Approach in the Field of Enkephalins, ANP and CCK" by Bernard P. Roques.

Tetrahedron Letters No. 52, pp. 4859–4862, 1976, "Regiospecific Versus Non–Regiospecific Photoinduced Ring–Enlargement of 3–Substituted 1–Iminopyridinium Ylides", by Jacques S. et al.

M.R.Chemistry, vol. 20, 1988, 471–474, "Synthesis and Spectroscopic Studies of 2–(1,1–Dimethylhydrazono)propyl Phosphonates" by Miguel Salazar et al.

The Journal of Organic Chemistry, vol. 35, No. 2, Feb. 1970, The Chemistry of Diazepines. The Photochemical Intramolecular 1,3–Dipolar Cycloaddition of Substituted 1–Ethoxycarbonyliminopyridinium Ylides, Tadashi Sasaki, et al.

Journal of Chemistry, 31, Nov. 1966, 3851–3852, "A Novel Synthesis of 1,5–Diphenylpyrazolone–3", by Henry W. Schiessl et al.

J. Prakt. Chem. [2] 110, 204, 1925, "Polyspirocyclische Komplexe des Palladiums mit Phosphor–Yliden", by Hubert Schmidbaur et al.

Liebigs Ann. Chem. 1982, 1304–1321, "The α–Helical Conformation of the Undecapeptide Boc–L–Ala–[Aib–Ala]$_2$–Glu(OBzl)–Ala–[Aib–Ala]$_2$–OMe: Synthesis, X–Ray Crystal Structure, and Conformation in Solution", by Heribert Schmitt.

Liebigs Ann. chem. 1988, 1025–1031, "Asymmetric Synthesis of Boc–L–Val–(R)–α–MePro–OMe, Boc–L–Val–(R)–Proome, and of Boc–L–Val–(R)–α–MePhe–OMe, Ac–L–Val–(R)–α–MePhe–OMe and Their Analogues. A New Strategy for the Synthesis of Non–Proteinogenic Dipeptides", by Ulrich Schollkopf.

Communications, Dec. 1981, pp. 969–971, "Asymmetric Syntheses via Heterocyclic Intermediates; VIII. Enantioselective Synthesis of (R)–α–Methyl–α–amino Acids using L–Valine as Chiral Auxiliary Reagent by Ulrich Schollkopf et al.

Angew. Chem., 90 (1978), Nr. 2, pp. 136–138, "Asymmetrische Syntheses von x–Alkyl–x–aminocarbon–sauren durch Alkylierung von 1–chiral–substituierten 2–Imidazonin–5–onen", by Von Ulrich Schollkopf et al.

Angew Chem. Int. Ed. Engl. 18 (1979), No. 11, Enantioselective Synthesis of α–Methyl–αaminocarboxylic Acids by Alkylation of the Lactim Ether of cyclo–(l–ala–l–Ala), by Ulrich Schollkopf et al.

Angew, Chem. Internat. Edit., vol. 14(1975), No. 8, "Applications of Field Desorption Mass Spectrometry in Inorganic Chemistry: Salts", by H.R. Schulten.

J. Org. Chem USSR, 1977, 13, 885, "Reaction of Acyl Nitrenes with Unsaturated Compounds", by V.P. Semenov et al.

Biophy.J., vol. 64, Apr. 1993, 1017–1028, "The permeation properties of small organic cations in gramicidin A channels", by Sang–Ah Seoh.

J.C.S. Chem. Comm., 1978, pp. 996–997, "The $3_{10}$ Helical Conformation of a Pentapeptide Containing a–Aminoisobutyric Acid (Aib): X–Ray Crystal Structure of Tos–(Aib)$_5$–OMe", by N. Shamala et al.

Biochemical and Biophysical Research Communications, vol. 79, No. 1, 1977, "The Crystal and Molecular Structure Of The Amino Terminal Tetrapeptide of Alamethicin. A Novel 310 Helical Conformation", by N. Shamala et al.

J.C.S. Chem.Comm., 1978, 996–997, "The $3_{10}$ Helical Conformation of a Pentapeptide Containing α–Aminoisobutyric Acid (Aib): X–Ray Crystal Structure of Tos–(Aib)5–OMe", by Narayanaswamy Shamala et al.

I–Pharmacology, vol. 108, 1988, p. 31589, "Regulation of carnitive–dependent metabolism of fatty acids in myocardium under the influence of 3–(2,2,2–tri–methylhydrazinium)propionate" Zh. Shutenko et al.

Chemical Abstracts, vol. 115, 1991, p. 45, "Regulation of the carnitive–dependent metabolism of fatty acids in the rat myocardium", Zh. Shutenko et al.

The Journal of Organic Chemistry, vol. 33, No. 4, Apr. 1968, "Aminimides. VI. Synthesis of Aminimides from Carboxylic Acid Esters, Unsymmetrically Disubstituted Hydrazines, and Epoxides", by R.C. Slagel.

Canadian Journal of Chemistry, vol. 45, 2625, (1967), "Aminimides. III. A convenient synthesis of isopropenyl isocyanate", by Robert C. Slagel et al.

Organic Preparations and Procedures Int. 13(1), 55–58, 1981, "Preparation of 2–Hydroxyethyldimethylamine Acylimides" by Robert J. Small.

J. Org. Chem., vol. 41, No. 9, 1976, 1555–1556, "Reaction of 1,1–Dibenzoyl–2,2–dimethylhydrazine with Methyl p–Toluenesulfonate", by Richard F. Smith.

J. Am. Chem. Cos., 1981, vol. 103, pp. 1493–1501, "Crystal Structures and Conformational Calculations of Fragments of Alamethicin Containing Aminoisobutyric" by G. David Smith.

Chemical Communications, 1965, 120, "The Pyrolysis and Photolysis of Trimethylamine Benzimide", by Richard F. Smith.

J. Org. Chem., vol. 59, No. 14, 1974, "Stevens Rearrangement of Carbamoylaminimides" by Richard F. Smith et al.

Chemistry Department of the University of Michigan, Sep. 1959, 1325–1332, vol. 24, "Nitroative Cleavage of N',N'–Dialkylhydrazides and Tertiary Amines", by Peter Smith et al.

Bull. Soc. Chem., France – 1969 No. 6, 2175–2179, "No. 382—Syntheses Photochimique de (1–H)–Diazepines–1,2" by Jacques Streith et al.

Chem. Ber. III, 780–790 (1978), "Pyrazolium–Betaine aus 1, 1–Dialkylhydrazinen und Acetylencarbonsaureestern", by Wolfgang Sucrow et al.

Journal of the American Chemical Society, 90:19, Sep. 11, 1968, "Novel Heterocyclic Syntheses from Azomethine Imides. 2–Unsubstituted Diazetidinones", by Ken'ichi Takeuchi, et al.

Chem. Pharm. Bull., vol. 31, 1983, 1378–1381, "1,3–dipolar Cycloaddition Reaction of 1–Methylperimidine 3–Ylides with Dimethyl Accetylenedierboxylate", by Yasumitsu Tamura et al.

J. Heterocyclic Chem., 9, Aug. 1972, 865, "Synthesis of 3–substituted N–Aminopyridinium Salts(I)", by Yasumitsu Tamura et al.

J.C.S. Perkin I, 1973, 2580–2583, "Synthesis and Thermal Reaction of 2,2–Diacyl–N–(1–pyridinio)vinyl–aminides: Formation of Pyrazolo[1,5–a]pyridines and Isoxazoles", by Yasumitsu Tamura et al.

Chem. Pharm.Bull., 19(6)1285–1286 1971, "The Photo Arrangement and Thermolysis of N–Benzoylimino–isoquinolinium and Quinolinium Betaines", by Yasumitsu Tamura et al.

Organic Preparations and Procedures 1(3), 217–219 (1969), "A convenient synthesis of 5–oxazolones. 2–phenyl–5–oxazolone" by Lloyd D. Taylor et al.

Polymer Letters, vol. 7, pp. 597–603(1969), "The Synthesis of Vinyl Peptide Monomers", by L.D. Taylor et al.

Journal of Polymer Science: Part C: Polymer Letters, vol. 24, 287–289 (1986), A Polymer whose Aqueous Solutions Show the Properties of Negative Thixotropy and Thermoreversible Gelation: (Poly–(Trimethylamine p–Vinylbenzimide), by LLoyd D. Taylor et al.

Makromol Chem., Rapid Commun. 3, 779–782(1982), "Synthesis of Poly(4,4–dimethyl–2–vinyl–5–oxazolone) an Interesting Material for Preparing Polymeric Agents", by Lloyd D. Taylor et al.

Polymer Letters, vol. 9, pp. 187–190(1971), "Synthesis and Polymerization of 2–vinyl–4,4–Dimethyl–5–Oxazolone" by L.D. Taylor et al.

Rubber Chem. Technology, 53, 1980, "Halogen–containing Aminimide Compounds as Tire Cord Adhesives", by P.E. Throckmorton et al.

Eur. J. Med. Chem.—Chem. Ther. 1982–17, N. 3, pp. 265–270, "Aminimides ethyleniques a action vasodilatatrice peripherique", by Mohamed Tichniouin et al.

Eur. J. Med. Chem., 1982, 17, No. 3, pp. 265–270, "Aminimides ethyleniques a action vasodilatatrice peripherique", by M. Tichniovin et al.

J. Chem. Soc. Perkin Trans. 1988, "Reactions of Some 1,3–Diaminonucleophiles with Azlactones" by Ahmad M. Tikdari et al.

Int. J. Peptide Protein Res. 22, 1983, 603–610, "Bioorganic stereochemistry", by Claudio Toniolo et al.

Biopolymers, vol. 22, 205–215(1983), Preferred Conformations of Peptides Containing α,α–Disubstituted α–Amino Acids, by Claudio Toniolo et al.

Bull Chem. Soc. Japan, 1980, 53, 1149, "Reaction of Ethyl Aziodoformate with Morpholines", by Teruko Tshuchida et al.

J. Chem. Soc., Chem Commun., 1982, 875–876, "Evidence for Amide Resonance observed in Cyclic N–Ammonio–imitates by X–Ray Photoelectron Spectroscopy", by Shinji Tsuchiya.

J. Chem. Soc. Perkin Trans. 11, 1993, "On the Nature of Nitrogen—Nitrogen Bonding in Cyclic Aminimides", by Shinji Tsuchiya.

Chem. Pharm. Bull. 31(12)4568–4572 1983, "Thermal Rearrangement of Cyclic Amine Ylides. III.[1)] Intramolecular Cyclization of 2–Ethynylpyridine N–Imides to 3–Azaindolizine Derivatives", by Takashi Tsuchiya et al.

J. Org. Chem., vol. 44, No. 16, 1979, 2850–2855, "On the Bond Character of N–Containing Ylides", by Shinji Tsuchiya et al.

Chem. Pharm. Bull., 30 (10)3757, 1982, "Studies on Diazepines. XVIII. Photochemical Synthesis of 3H–1,3–Benzodiazepines from Quinoline N–Acylimides", by Takashi Tsuchiya et al.

Bull Chem. Soc. Japan, 1983, 2073, "Double Cycloaddition Reaction of Imidazolium Methylides. Intermolecular 1,3–Dipolar and Intramolecular Diels–Alder Cycloaddition Reactions", by Otohiko Tsuge et al.

Journal of Chemistry, 1966, vol. 31, 1704–1707, "Cyclic Aminimides", by William S. Wadsworth, Jr.

Journal American Chemical Society, vol. 82, 1960, 5718–5721, "The Rearrangement of 1,1–Dimethyl–1–p–nitrobenzylamine–2–acetamide", by S. Wawzonek.

Journal of Chemistry, 28, 1963, vol. 28, 2376–2377, The Resolution of 1–Ethyl–1–methyl–1–p–nitrobenzylamine–2–acetamide", by S. Wawzonek et al.

J.Org.Chem., Sep. 1965, 3031–3033, "The Rearrangement of 1–Methyl–1–acetylimide–2–phenylpyrrolidine", by S. Wawzonek et al.

Organic Preparations and Procedures Int. 8(5), 215–217 (1976), "Electrolytic Preparation of bis–Dimethyl–2–Hydroxypropylamineazobenzimides", by S. Wawzonek et al.

J. Med. Chem., 1982, 25, 720–723, "Synthesis of N–[[(Substituted–phenyl)carbonyl]amino]–1,2,3,6–tetrahydropyridines with Analgesic and Hyperglycemic Activity", by Jupita M. Yeung.

J. Med. Chem, 1987, 30, 104–108, "Synthesis of N–(3, 6–Dihydro–1(2H)–pyridinyl)benzamides with Hyperglycemic–Hypoglycemic Activity", by Jupita M. Yeung et al.

J. Med. Chem. 1982, 25, 191–195, "Synthesis of N–(Carbonylamino)–1,2,3,6–tetrahydropyridines with Analgesic, Antiinflammatory, and Hyperglycemic Activity", by Jupita M. Yeung et al.

B.M. Culbertson, R.E. Frais, and D. Grate, Polymer Science: Part A–1, No. 12, vol. 9, 3453–3470, 1971.

M. Liler et al., "Mono– and Di–protonation Sites in N–Ammonio–amidates: a Spectroscopic Study", J. Chem. Soc., Perkin II (1977), pp. 909–914.

B. Zeeh et al., "Ein einfache Isoindol–Synthese", Syntheisis (1972), pp. 45–46.

W.J. McKillip et al., "Aminimides. II. A one–step synthesis of aminimides from carboxylic acid esters", Canadian Journal of Chemistry, vol. 45 (1967), pp. 2619–2623.

HYDROXYETHYL AMINIMIDES

CROSS REFERENCE TO RELATED APPLICATIONS

This is a division of application Ser. No. 08/326,573 filed Oct. 20, 1994, now U.S. Pat. No. 5,734,082.

BACKGROUND OF THE INVENTION

Recent research in the fields of separation technology and pharmaceutical compounds reveals that many reactions between chemical compounds result from the three dimensional structure, and the molecular interactions between different compounds. A complementary structural relationship has been tied to a particular chemical compounds ability to react with a second chemical compound (see, for example, "The Concept of Molecular Structure in Structure-Activity Relationship Studies and Drug Design", Testa et al., Medicinal Research Reviews, 1991, Vol. 11, No. 1). The present invention relates to hydroxyethyl aminimide chemical structures which can be used as molecular scaffolding on which to hang different substituent groups. By varying the different substituent groups on an aminimide chemical backbone as disclosed herein it is possible to develop chemical compounds having a complementary structural and molecular relationship to a target compound, enzyme, molecular recognition site or receptor. Use of the present invention represents an improvement in both the cost and time efficiency of identifying lead compounds.

Hydroxyethyl aminimides (herein after referred to as aminimides), can be prepared from the one-step reaction of an ester or acid chloride, a hydrazine, and an epoxide according to a method such as that disclosed by Middleton, U.S. Pat. No. 3,963,776 and Culbertson, U.S. Pat. No. 3,963,703. Alternatively, hydroxyethyl aminimides can be formed from the alkylation of a disubstituted hydrazide through the opening of an epoxide such as by the reactions disclosed in Grimm, U.S. Pat. No. 3,850,969. An extensive discussion of aminimides including their preparation and uses is set forth in PCT application PCT/US93/12612 filed Dec. 28, 1993 in the name of ArQule Partners, L.P., which is herein incorporated by reference in its entirety.

Aminimides have a diversity of properties, and are known to be useful as surfactants, (see, for example, Falk, U.S. Pat. No. 4,102,916, and Middleton, U.S. Pat. No. 3,963,776), resin hardeners, precursors to isocyanates (see, for example, Brutchen, U.S. Pat. No. 3,898,087), in the formation of polyurethanes (see, for example, Kresta, U.S. Pat. No. 4,067,830) and polyisocyanurates (see Kresta, U.S. Pat. No. 3,925,284).

Much less is known about the biological activity of aminimides. Kabara has shown that specific aliphatic derived dimethyl-hydroxyethyl aminimides possess antimicrobial (see U.S. Pat. Nos. 4,189,481 and 4,217,364) and antifungal properties (see U.S. Pat. Nos. 3,934,029 and 3,934,031). L. Boutis, et al., have observed antineoplastic activity (*Current Chemotherapy*, 1978, 2, 1213–1216), while M. Tichniouin, et al. demonstrated that certain dimethyl-hydroxyethyl aminimides possess a noticeable vasodilating activity (*Eur. J. Med. Chem.*, 1982, 17, 265–270). Yet, to date, no one has used an aminimide moiety, and, in particular, a hydroxyethyl aminimide moiety as a peptide isostere in the design of pharmacologically active compounds.

The present invention relates to the use of hydroxyethyl aminimides as isosteres in the design and synthesis of chemical compounds capable of binding to an active site of a receptor or enzyme or to a molecular recognition site in, for example, separation chemistry.

SUMMARY OF THE INVENTION

It is an object of this invention to provide a novel class of hydroxyethyl aminimide compounds useful for their complementary properties to molecular recognition sites and/or enzymes.

Another object of this invention is to provide a method of making chemical compounds which are complementary to other chemical compounds.

Other objects of this invention will be apparent to those skilled in the art to which this invention applies.

The objects of this can be accomplished using a chemical backbone having the following chemical formula I:

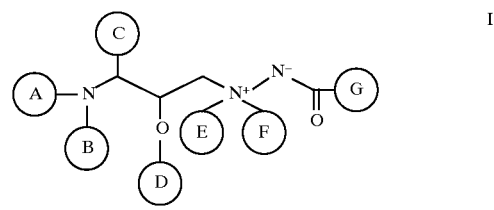

In compounds having chemical formula I, structural diversity elements A, B, C, E, F and G are the same or different, and each is selected from the group consisting of a chemical bond, hydrogen, an electrophilic group, a nucleophilic group, an amino acid derivative, a nucleotide derivative, a carbohydrate derivative, an organic structural motif, a reporter element, an organic moiety, optionally containing a polymerizable group, and a macromolecular component. Optionally, the structural diversity elements A, B, C, E, F and G are connected to each other or to other structures. In addition, structural diversity element D is selected from the group consisting of hydrogen, branched or straight chain lower alkyl having from 1–8 carbon atoms, ether and ester groups, and n is an integer greater than 0.

DETAILED DESCRIPTION OF THE INVENTION

Figure 1:
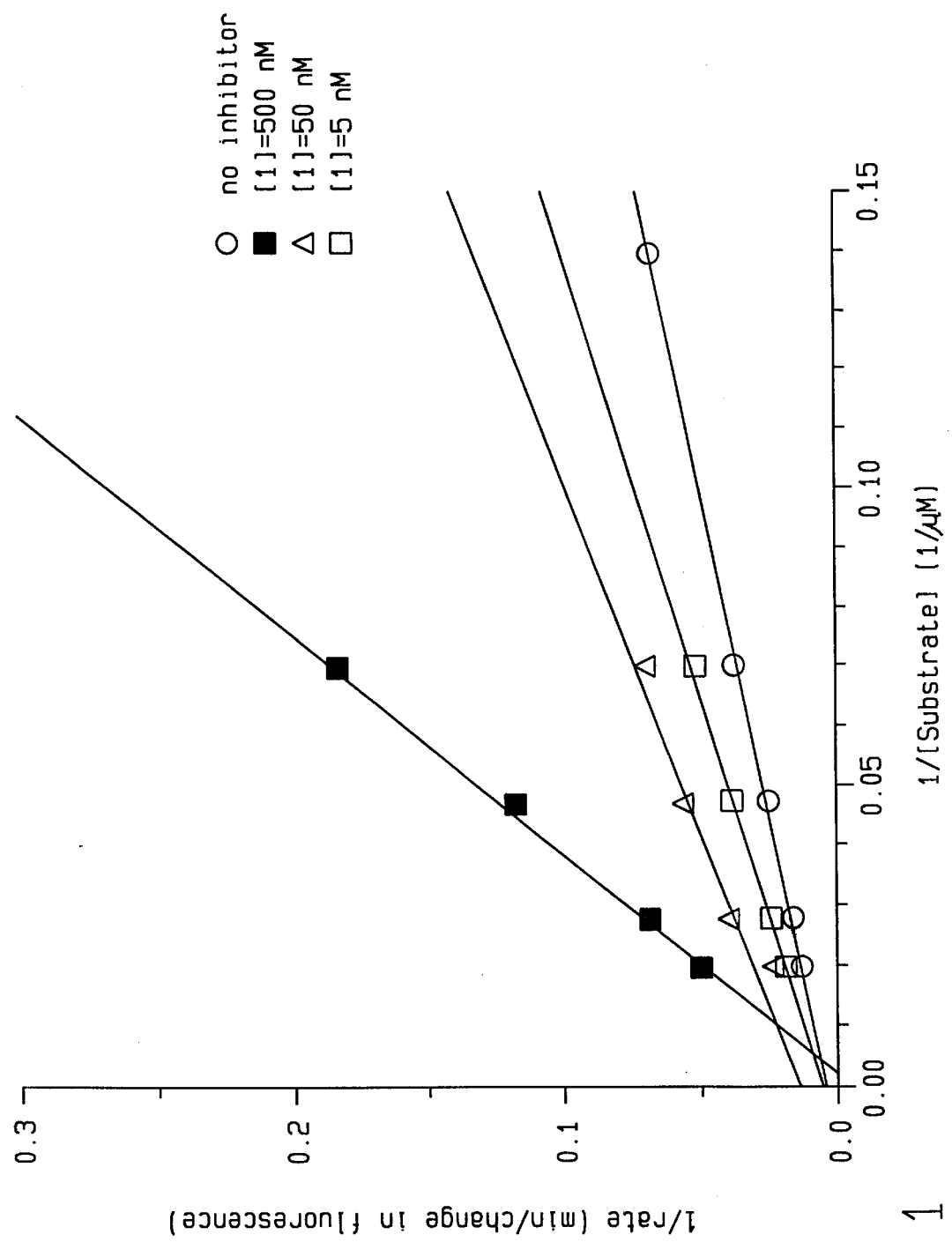
FIG. 1 is a graph of a Lineweaver-Burk plot for Compound IA of the example.
Figure 2:
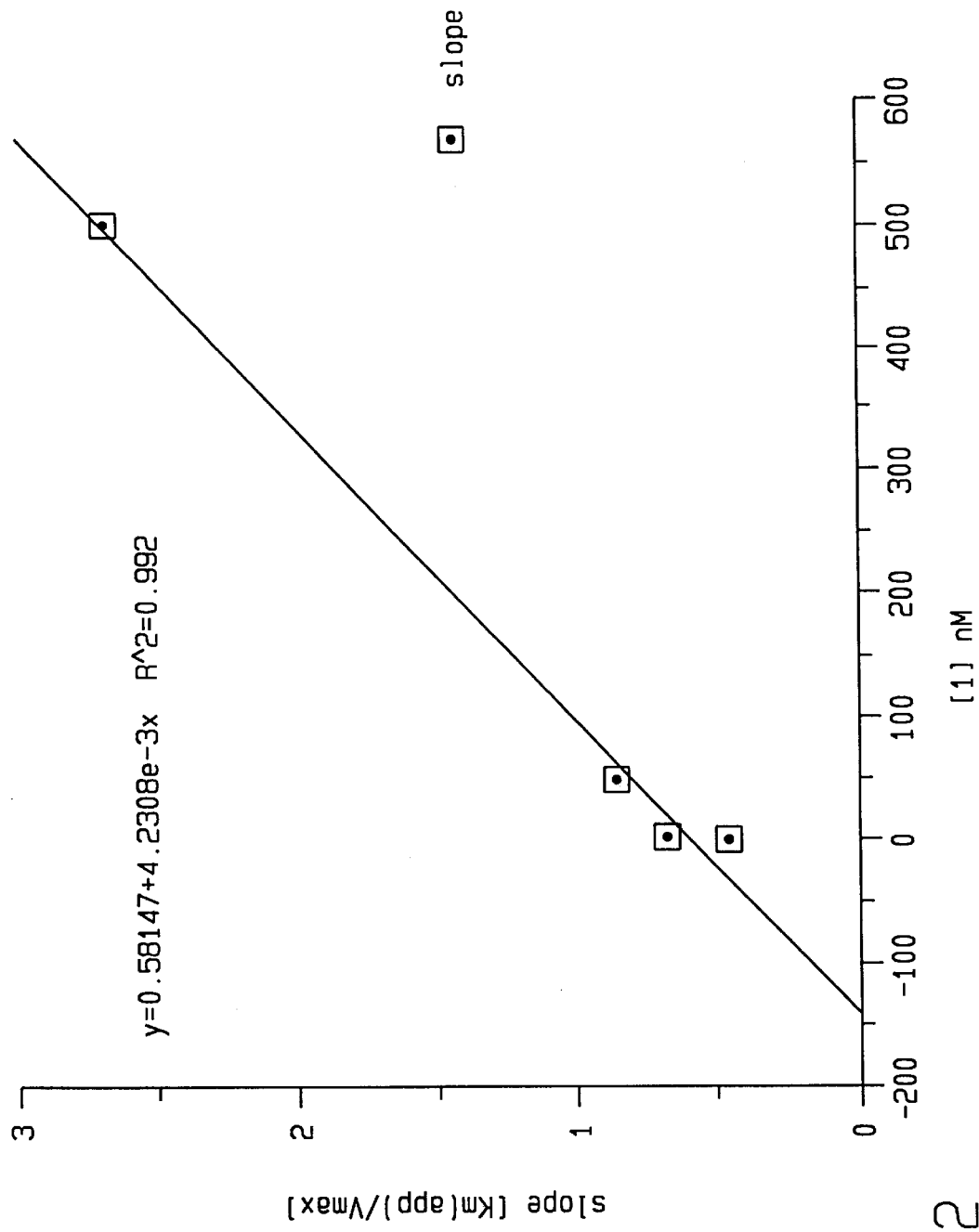
FIG. 2 is a replot of the slopes of the Lineweaver-Burk plot for Compound IA of the example.

The present invention relates to the use of hydroxyethyl aminimides and to their use as molecular recognition agents in the design and synthesis of compounds for use as biologically active compounds and in separations technology, such as a peptide isostere.

A peptide isostere is a moiety that, when substituted for the peptide bond, will confer upon the analog certain stearic and/or electronic configurations similar to the parent compound, thereby allowing the analog to possess biological properties similar to the parent compound. However, the isostere is designed to be resistant to degradation by the same pathways as a nominal peptide.

For the purposes of the present invention, the term "complementary" is given the definition currently used in the chemical and biochemical arts that refers to a close three dimensional and/or molecular interaction relationship between two different compounds, which is analogous to a lock and key.

The term "backbone" is defined, for the purpose of the present invention, as an organic chain of elements that can be substituted with one or more structural diversity elements to yield a chemical compound or a class of chemical compounds which are complementary to a second chemical compound or class of chemical compounds.

The hydroxyethyl aminimides of the present invention have a chemical backbone with the following chemical formula I:

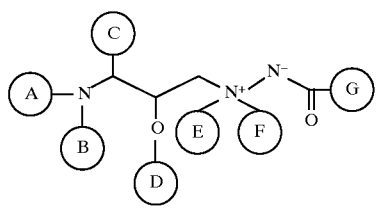

wherein:
structural diversity elements A, B, C, E, F and G are the same or different, and each is selected from the group consisting of a chemical bond, hydrogen, electrophilic group, a nucleophilic group, an amino acid derivative, a nucleotide derivative, a carbohydrate derivative, an organic structural motif, a reporter element, an organic moiety, optionally containing a polymerizable group, and a macromolecular component. Optionally, the structural diversity elements A, B, C, E, F and G are connected to each other or to other structures. In addition, structural diversity element D is selected from the group consisting of hydrogen, branched or straight chain lower alkyl having from 1–8 carbon atoms, ether and ester groups, and n is an integer greater than 0. For this invention, it is understood that each integer that n can be, represents a structural embodiment of the backbones of this invention. Thus, each integer from 1 to at least about 100,000 to 500,000 is expressly disclosed as preferred embodiments of the present invention. Higher values of n can be used, if desired, for specialty polymers.

The particular structural diversity elements can vary greatly, depending upon the specific compound to be prepared.

One of ordinary skill in the chemical arts is well aware of the bonding properties, and capabilities, of these elements, and can easily select the appropriate element for attachment to the particular location on the backbone. Thus, the backbone represents a very valuable tool for constructing any one of a wide variety of compounds, and it represents an essential feature of this invention.

The synthesis and design of aminimide compounds is well known in the art and is detailed for example in PCT/US93/12612 referenced above. The aminimide compound of the present invention can be synthesized in a similar manner by many routes. It is well known in the art of organic synthesis that many different synthetic protocols can be used to prepare a given compound. Different routes can involve more or less expensive reagents, easier or more difficult separation or purification procedures, straightforward or cumbersome scale-up, and higher or lower yield. The skilled synthetic organic chemist knows well how to balance the competing characteristics of synthetic strategies. Thus the compounds of the present invention are not limited by the choice of synthetic strategy, and any synthetic strategy that yields the compounds described above can be used.

Hydroxyethyl aminimide compounds can be synthesized by a number of different synthetic routes. A useful and versatile general synthesis for these aminimides involves the one-pot reaction of an epoxide, a disubstituted hydrazine, and an ester in a hydroxylic solvent, such as water or an alcohol. The reaction is typically allowed to proceed at room temperature over a period of several hours to several days. The structural diversity elements of the claimed compounds are typically provided through the appropriate choice of the substituents on the epoxide, hydrazine and ester starting materials. In addition, the hydroxyethyl aminimide compounds of the invention obtained by this reaction can be modified by subsequent reaction to obtain the desired structural diversity elements in the compounds.

The reaction of an epoxide, a disubstituted hydrazine, and an ester that produces aminimide compounds may be generally represented by the following equation.

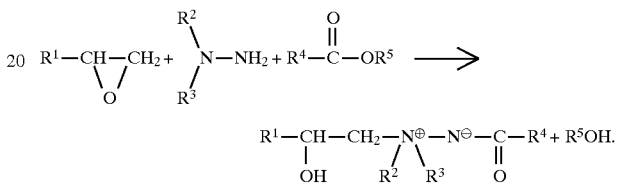

Structural elements $R^1$, $R^2$, $R^3$, and $R^4$, are selected to provide the structural diversity elements of the desired hydroxyethyl aminimide compounds. Therefore, the number and type of structural diversity elements that can be incorporated into the present compounds are only limited by the availability of appropriate starting materials. Many different epoxide, disubstituted hydrazine, and ester compounds having various substituents to form structural diversity elements in the final product are commercially available or can be synthesized by those of ordinary skill in the art. In addition, commercially available epoxides, hydrazines, and esters can be easily modified to provide additional structural diversity elements on the desired compounds.

To obtain the hydroxyethyl aminimide compounds of formula I,

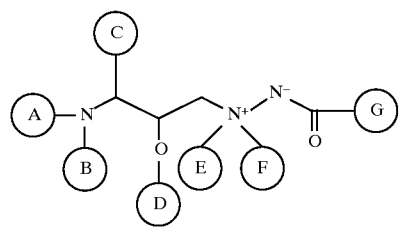

the $R^1$— group obtained from this reaction should have the following structure.

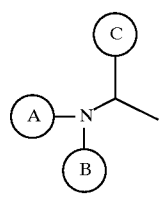

Also, the epoxide used as a starting material in the reaction would have the following structure.

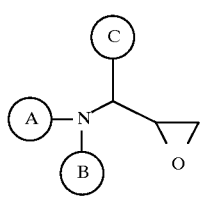

An example of the synthesis of such an epoxide is discussed by Luly et al., *J. Org. Chem.*, 1987, 52, 1487, and follows the following reaction scheme.

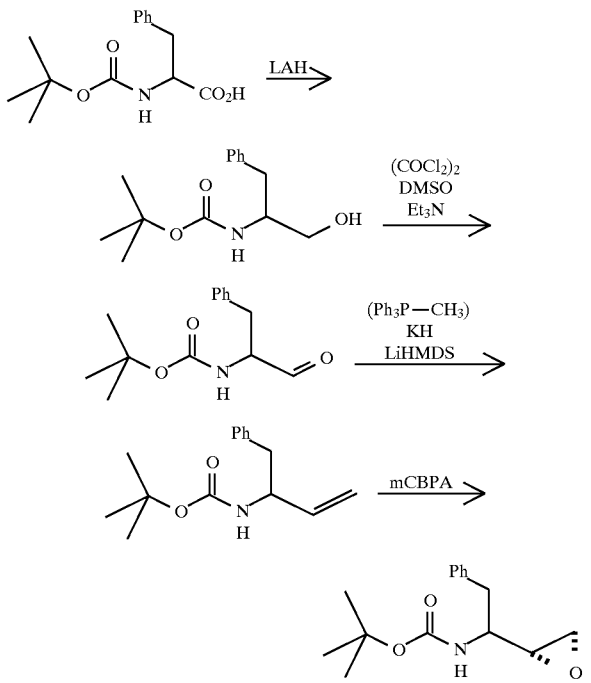

In addition, to obtain a structural diversity element D which is other than a hydrogen atom, the —OH group on the backbone can be alkylated with a suitable alkylating agent, as shown in the following reaction.

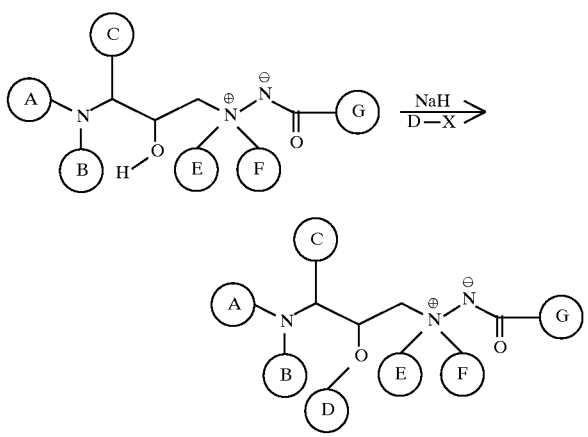

The alkylating agents required to provide a large variety of different groups as diversity agent D are readily available or can be synthesized from available materials.

Accordingly, any known method of producing the subject hydroxyethyl aminimide compounds can be used to produce a wide variety of chiral aminimide conjugates of the following general structures:

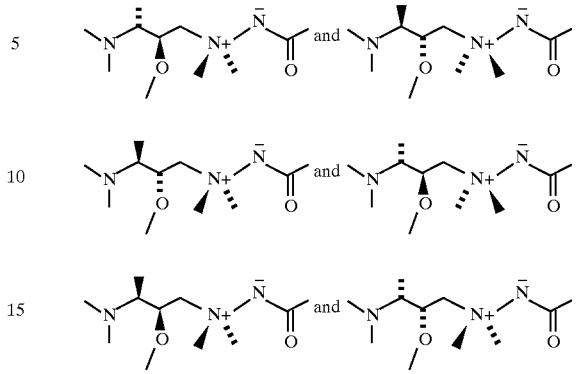

The structural diversity elements A, B, C, E, F and G may be the same or different, may be of a variety of structures and may differ markedly in their physical or functional properties, or may be the same; they may also be chiral or symmetric. The structural diversity elements A, B, C, E, F and G are preferably selected from:

1) Amino acid derivatives of the form $(AA)_n$, which would include, for example, natural and synthetic amino acid residues, where n is 1, including all of the naturally occurring alpha amino acids, especially alanine, arginine, asparagine, aspartic acid, cysteine, glutamine, glutamic acid, glycine, histidine, isoleucine, leucine, lysine, methionine, phenylalanine, proline, serine, threonine, tryptophan, and tyrosine; the naturally occurring disubstituted amino acids, such as amino isobutyric acid, and isovaline, etc.; a variety of synthetic amino acid residues, including alpha-disubstituted variants, species with olefinic substitution at the alpha position, species having derivatives, variants or mimetics of the naturally occurring side chains; N-substituted glycine residues; natural and synthetic species known to functionally mimic amino acid residues, such as statine, bestatin, etc. Amino acid derivatives of the form $(AA)_n$ also include peptides, where n is from 2 to about 30, constructed from the amino acids listed above, such as angiotensinogen and its family of physiologically important angiotensin hydrolysis products, as well as derivatives, variants and mimetics made from various combinations and permutations of all the natural and synthetic residues listed above; polypeptides, where n is from about 31 to about 70, such as big endothelin, pancreastatin, human growth hormone releasing factor and human pancreatic polypeptide; proteins, where n is greater than about 70, including structural proteins such as collagen, functional proteins such as hemoglobin, regulatory proteins such as the dopamine and thrombin receptors, and depsipeptides, which include derivatives of amino acids, peptides, polypeptides and proteins that contain a hydroxy and amino acid residual linked by amide or ester bonds, and include peptide-related compounds such as azinothricin, actinomycin, and echinomycin.

2) Nucleotide derivatives of the form (NUCL), which include natural and synthetic nucleotides, where is 1, such as adenosine, thymine, guanidine, undine, cytosine, derivatives of these and a variety of variants and mimetics of the purine ring, the sugar ring, the phosphate linkage and combinations of some or all of these; nucleotide probes, where n is from 2 to about 25, and oligonucleotides, where n is greater than about 25, including all of the various possible homo- and hetero-synthetic combinations and permutations of the naturally occurring nucleotides derivatives and variants containing synthetic purine or pyrimidine species, or mimics of these, various sugar ring mimetics, and a wide variety of alternate backbone analogs, including, but not limited to phosphodiester, phosphorothionate, phosphorodithionate, phosphoramidate, alkyl phosphotriester, sulfamate, 3'-thioforimacetal, methylene (methylimino), 3-N-carbamate, morpholino carbamate and peptide nucleic acid analogs.

3) Carbohydrate derivatives of the form $(CH)_n$, which include natural physiologically active carbohydrates, related compounds, such as glucose, galactose, sialic acids, β-D-glucosylamine and nojorimycin, which are both inhibitors of glucosidase, pseudo sugars, such as 5α-carba-2-D-galactopyranose, which is known to inhibit the growth of Klebsiella pneumonia (n=1); synthetic carbohydrate residues and derivatives of these (n=1) and all of the complex oligomeric permutations of these as found in nature, including high mannose oligosaccharides, the known antibiotic streptomycin (n>1).

4) A naturally occurring or synthetic organic structural motif, where the term "motif" is defined as an organic molecule having or containing a specific structure that has molecular recognition characteristics, such as a molecule having a complementary structure to an enzyme active site. Naturally occurring or synthetic organic structural motifs include any of the well known basic structures of pharmaceutical compounds including pharmacophores, or metabolites thereof. These basic structures include beta-lactams, such as penicillin, known to inhibit bacterial cell wall biosynthesis, dibenzazepines, known to bind to CNS receptors and used as antidepressants, and polypeptide macrolides, known to bind to bacterial ribosymes. These structural motifs are generally known to have specific desirable binding properties to ligand acceptors.

5) Reporter elements, such as a natural or synthetic dye or a residue capable of photographic amplification, which possesses reactive groups that may be synthetically incorporated into the aminimide structure or reaction scheme, and may be attached through the groups without adversely interfering or affecting with the reporting functionality of the group. Preferred reactive groups are amino, thio, hydroxy, carboxylic acid, carboxylic acid ester, particularly methyl ester, acid chloride, isocyanate alkyl halides, aryl halides and oxirane groups.

6) An organic moiety containing a polymerizable group, such as a double bond, or other functionalities capable of undergoing condensation polymerization or copolymerization. Suitable groups include vinyl groups, oxirane groups, carboxylic acids, acid chlorides, esters, amides, azlactones, lactones and lactams. Other organic moieties may also be used.

7) A macromolecular component, such as a macromolecular surface or structures, which may be attached to the aminimide modules via the various reactive groups outlined above, in a manner where the binding of the attached species to a ligand-receptor molecule is not adversely affected, and the interactive activity of the attached functionality is determined or limited by the macromolecule. Examples of macromolecular components include porous and non-porous inorganic components, such as, for example, silica, alumina, zirconia, titania and the like, which are commonly used for various applications, such as normal and reverse phase chromatographic separations, water purification, and pigments for paints, etc., porous and non-porous organic macromolecular components, including synthetic components, such as styrene-divinyl benzene beads, various methacrylate beads, PVA beads, and, the like, commonly used for protein purification, water softening and a variety of other applications, natural components such as native and functionalized celluloses, such as, for example, agarose and chitin, sheet and hollow fiber membranes made from nylon, polyether sulfone or any of the materials mentioned above. The molecular weight of these macromolecules may range from about 1000 Daltons to as high as possible. They may take the form of nano-particles (dp=100–1000 Angstroms), latex particles (dp=1000–5000 S Angstroms), porous or non-porous beads (dp=0.5–1000 microns), membranes, gels, macroscopic surfaces or functionalized or coated versions or composites.

The structural diversity elements A, B, C, E, F and G may also be a chemical bond to a suitable organic moiety, a hydrogen atom, an organic moiety that contains a suitable electrophilic group, such as an aldehyde, ester, alkyl halide, ketone, nitrile, epoxide or the like, a suitable nucleophilic group, such as a hydroxyl, amino, carboxylate, amide, carbanion, urea or the like, or one of the structural diversity elements C and/or D groups defined below. In addition, structural diversity elements A, B, C, D, E, F and/or G may join to form a ring, bi-cyclic or tri-cyclic ring system, or a structure that connects to the ends of the repeating unit of the compound defined by the preceding formula, or may be separately connected to other moieties.

A more generalized structure of the composition of this invention can be represented by the following structural formulas:

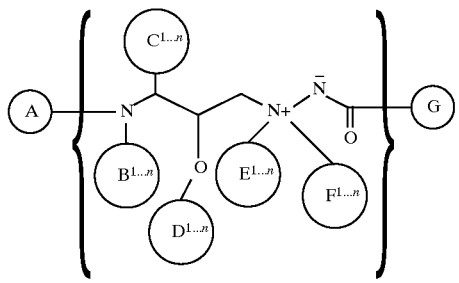

wherein:

a. at least one of the structural diversity elements A, B, C, E, F and G are as defined above, are optionally connected to each other or to other bonds, and/or may each represent a chemical bond or one or more atoms of carbon, nitrogen, sulfur, oxygen, phosphorus, silicon or combinations thereof;

b. structural diversity elements A, B, C, E, F and G are the same or different and each represents A, B, E, cyano, nitro, halogen, oxygen, hydroxy, alkoxy, thio, straight or branched chain alkyl, carbocyclic aryl and substituted or heterocyclic derivatives thereof, wherein structural diversity elements E and F may be different in adjacent n units, and have a selected stereochemical arrangement about the carbon atom to which they are attached;

c. A and G may be a chemical bond or a connecting group that includes a terminal carbon atom for attachment to the quaternary nitrogen and G may be different in adjacent n units; and d. n is an integer greater than 0.

As used herein, the phrases "linear chain" and "branched chained" alkyl groups mean any substituted or unsubstituted acyclic carbon-containing compounds, including alkanes, alkenes and alkynes. Alkyl groups having up to 30 carbon atoms are preferred. Examples of alkyl groups include lower alkyl, for example, methyl, ethyl, n-propyl, iso-propyl, n-butyl, iso-butyl or tert-butyl; upper alkyl, for example, octyl, nonyl, decyl, and the like; lower alkylene, for example, ethylene, propylene, propyldiene, butylene, butyldiene; upper alkenyl such as 1-decene, 1-nonene, 2,6-dimethyl-5-octenyl, 6-ethyl-5-octenyl or heptenyl, and the like; alkynyl such as 1-ethynyl, 2-butynyl, 1-pentynyl and the like. The ordinary skilled artisan is familiar with numerous linear and branched alkyl groups, which are within the scope of the present invention.

In addition, such alkyl group may also contain various substituents in which one or more hydrogen atoms has been replaced by a functional group. Functional groups include but are not limited to hydroxyl, amino, carboxyl, amide, ester, ether, and halogen (fluorine, chlorine, bromine and iodine), to mention but a few. Specific substituted alkyl groups can be, for example, alkoxy, such as methoxy, ethoxy, butoxy, pentoxy, and the like, polyhydroxy such as 1,2-dihydroxypropyl, 1,4-dihydroxy-l-butyl, and the like; methylamino, ethylamino, dimethylamino, diethylamino, triethylamino, cyclopentylamino, benzylamino, dibenzylamino, and the like; propionic, butanoic, or pentanoic acid groups, and the like; formamido, acetamido, butanamido, and the like, methoxycarbonyl, ethoxycarbonyl or the like, chloroformyl, bromoformyl, 1,1-chloroethyl, bromoethyl, and the like, or dimethyl or diethyl ether groups or the like.

As used herein, substituted and unsubstituted carbocyclic groups of up to about 20 carbon atoms means cyclic carbon-containing compounds, including, but not limited to cyclopentyl, cyclohexyl, cycloheptyl, adamantyl, and the like. Such cyclic groups may also contain various substituents in which one or more hydrogen atoms has been replaced by a functional group, for example, in a specific embodiment, structural diversity element A is cyclohexanol. Such functional groups include those described above, including the lower alkyl groups. The cyclic groups of the invention may further comprise a hetero-atom.

As used herein, substituted and unsubstituted aryl groups means groups containing an aromatic hydrocarbon ring bearing a system of conjugated double bonds, comprising 4p minus 2 pi bond electrons, where p is an integer equal to or greater than 1. Examples of aryl groups include, but are not limited to, phenyl, naphthyl, anisyl, toluyl, xylenyl and the like. According to the present invention, aryl also includes aryloxy, aralkyl, aralkyloxy and heteroaryl groups, e.g., pyrimidine, morpholine, piperazine, piperidine, benzoic acid, toluene or thiophene and the like. These aryl groups may also be substituted with any number of a variety of functional groups. In addition to the functional groups described above functional groups on the aryl groups include nitro groups.

As mentioned above, structural diversity elements can also represent any combination of alkyl, carbocyclic or aryl groups; for example, 1-cyclohexylpropyl, benzylcyclohexylmethyl, 2-cyclohexyl-propyl 2,2-methylcyclohexylpropyl, 2,2-methylphenylpropyl, 2,2-methylphenybutyl, and the like.

In one embodiment of the invention, at least one of A, B, C, D, E, F and G represents, an organic or inorganic macromolecular surface. Examples of preferred macromolecular surfaces include ceramics, such as silica and alumina, porous and non-porous beads, polymers, such as a latex in the form of beads, membranes, gels, macroscopic surfaces or coated versions or composites or hybrids thereof. This functionalized surface may be represented as follows.

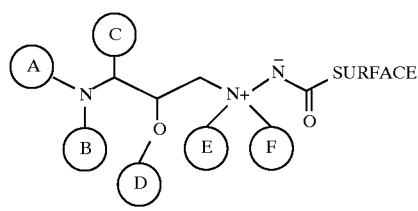

In a further embodiment of the invention, the above roles of diversity elements A and G are reversed, so that G is the substituent selected from the foregoing list and A represents a functionalized surface, as shown below.

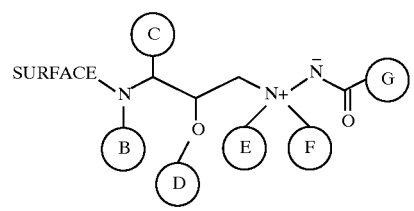

In a further embodiment of the invention, the above roles of diversity elements A and C are reversed, so that A is the substituent selected from the foregoing list and C represents a functionalized surface, as shown below.

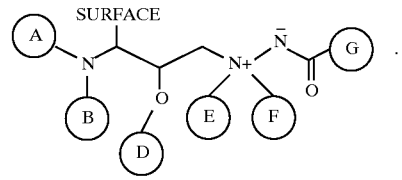

In a third preferred embodiment of the invention, either diversity elements A, B, E, two, three or all four contain one or more double bonds capable of undergoing free-radical polymerization or co-polymerization to produce achiral or chiral oligomers, polymers, copolymers, etc.

From the preceding, it is seen that the skilled artisan can design a particular compound in an attempt to achieve a desired goal. In the area of pharmaceuticals, for example, the backbone can be used as a starting point for attachment of a wide variety of diversity elements. The pharmacological activity of the resulting compounds can be easily and accurately screened, since the final structure of the compound is predictable and highly controlled.

Methods of screening or testing hydroxyethyl aminimide compounds for their reactivity and/or complementary nature with respect to a second chemical compound or class of compounds or enzyme, molecular recognition structure receptor is detailed in U.S. patent application Ser. No. 08/248,263 by Joseph C. Hogan, filed May 23, 1994, the entire content of which is specifically incorporated by reference herein.

The human immunodeficiency virus (HIV) has been implicated as the causative agent of acquired immune deficiency syndrome (AIDS) (see Popovic, et al., *Science*, 1984, 198, 497). The RNA genome of the HIV retrovirus encodes an aspartic protease known as the HIV-1 protease (see Kramer, H. A., et al., *Science*, 1986, 231, 1580). This protease is required for malitration and proliferation of the infectious virion. The role of the HIV-1 protease is to cleave, viral precursor proteins, in particular the Gag and Pol precursor proteins, into their active forms (see Darke, P. L.

et al., *Biochem. Biophys. Res. Comm.*, 1988, 156, 297). The HIV-1 protease is formed by the homodimerization of a 99 amino acid polypeptide; the active site of the protease is at the interface of the two subunits, with each subunit contributing one of the essential aspartic acid residues required for catalysis. The X-ray crystal structure of the HIV-1 protease has been solved and shows that the dimer structure is of $C_2$ symmetry in its unbound form (see Navia, M. A., et al., *Nature*, 1989, 337, 615). The structure clearly illustrates the extended active site of the protein, which incorporates processing site of S4-S3' (using the subsite nomenclature of Schechter and Berger, *Biochem. Biophys. Res. Comm.*, 1967, 27, 157). Independent substrate cleavage assays have indicated that substrate specificity of HIV-1 protease is significantly determined by subsites S2-S2' (see Pettit, S. C., et al. *Persp. in Drug Disc. Des.* 1993, 1, 69).

To date, numerous inhibitors of HIV-1 protease have been reported in the literature (see, for instance, Wlodawer, A.; Erickson, J. W., *Annu. Rev. Biochem.*, 1993, 62, 543). In certain examples, co-crystal structures of the protein/inhibitor complex have been solved, for example see C. L. Waller et al., *J. Med. Chem.*, 1993, 36, 4152–4160, allowing researchers to better understand the structure/activity relationships of the active inhibitors. Approaches towards structure-based inhibitor design have taken three routes: 1. transition-state analog inhibitors (see Grobelny, D., et al., *Biochem. Biophys. Res. Comm.*, 1990, 169, 1111); 2. substrate analog inhibitors (see Moore, M. L.; Dreyer, G. B., *Persp. in Drug Disc. Des.* 1993, 1, 85); and, 3. de novo designed inhibitors (see Lam, P. Y. S., et al., *Science*, 1994, 263, 380). In the design of transition-state analogues, researchers have attempted to replace the scissile amide bond with a non-hydrolyzable peptide isostere. A selection of successful inhibitor designs is illustrated in Table 1. Some of the more potent inhibitors of HIV-1 protease reported are shown in Table 2.

TABLE 1

Examples of transition-state isosteres employed as inhibitors of proteases.

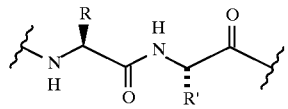

Normal Peptide

TABLE 1-continued

Examples of transition-state isosteres employed as inhibitors of proteases.

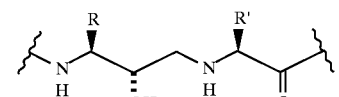

Hydroxyethylamine

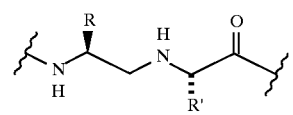

Reduced Amide

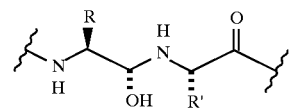

Hydroxethylene

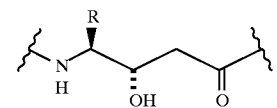

Statine

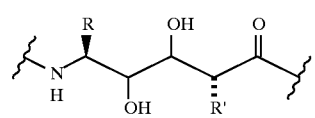

Dihydroxyethylene

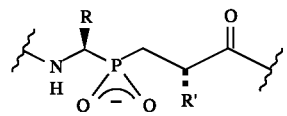

Phosphinate

Table 1: Examples of transition-state isosteres employed as inhibitors of proteases.

TABLE 2

Previous Inhibitors of HIV-1 protease.

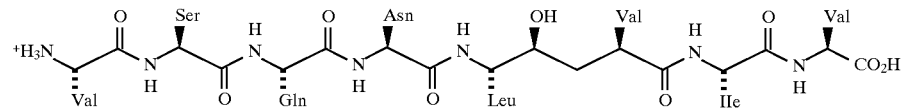

U-845548e   $K_i$ < 1 nM

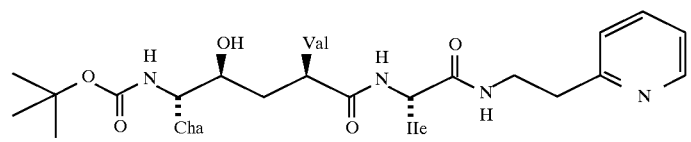

Ro-31-8588   $K_i$ = 0.3 nM

TABLE 2-continued

Previous Inhibitors of HIV-1 protease.

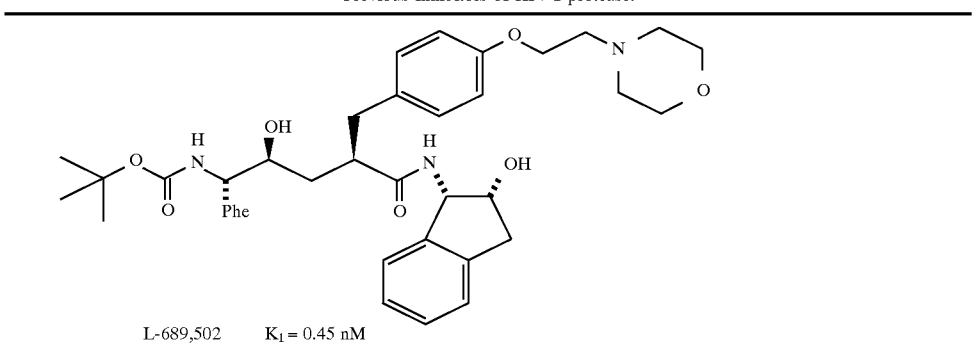

L-689,502    $K_i = 0.45$ nM

This present invention provides a novel transition-state analog inhibitor structure, which is an effective antagonist of the HIV-1 protease. In this peptide isostere, the scissile amide bond has been replaced with an aminimide linkage as illustrated in Table 3. Among the advantages of using an aminimide isostere are their ease of syntheses, and the ability to modify the target structures in a modular fashion by varying either the epoxide, hydrazine, or ester components used in the syntheses of new compounds. Furthermore, the aminimide moiety confers an increase water solubility of the synthesized compounds.

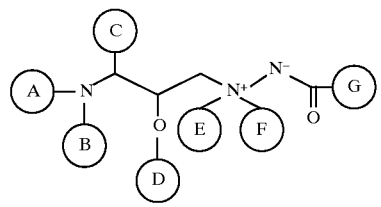

I

This prospective inhibitor I was designed using a model based on data from previous inhibition studies with HIV-1 protease. Compound I was modeled in the active-site of HIV-1 protease using the crystallographic data of the protein complexed with the inhibitor U-855488e (Brookhaven PDB identification code 8HVP). Energy refinements of the inhibitor in the presence of the fixed protein and in vacuo showed that no large conformational changes in the inhibitor were required in order to adopt the bound conformation.

EXAMPLES

In order to exemplify the results achieved using the chemical backbone of the present invention, the following examples are provided without any intent to limit the scope of the instant invention to the discussion therein, all parts are by weight unless otherwise indicated.

Example 1

The following is one example of the utility of a hydroxyethyl aminimide moiety being used as a motif for the design of complementary molecular structures.

Experimental: Synthesis

Synthesis of compound I required the three building blocks for the aminimide: 1. The enantiomerically pure t-butoxycarbonyl (t-BOC) protected epoxide (1), derived from phenylalanine; 2. the benzyl methyl hydrazine (2) and 3. methyl benzoate (3).

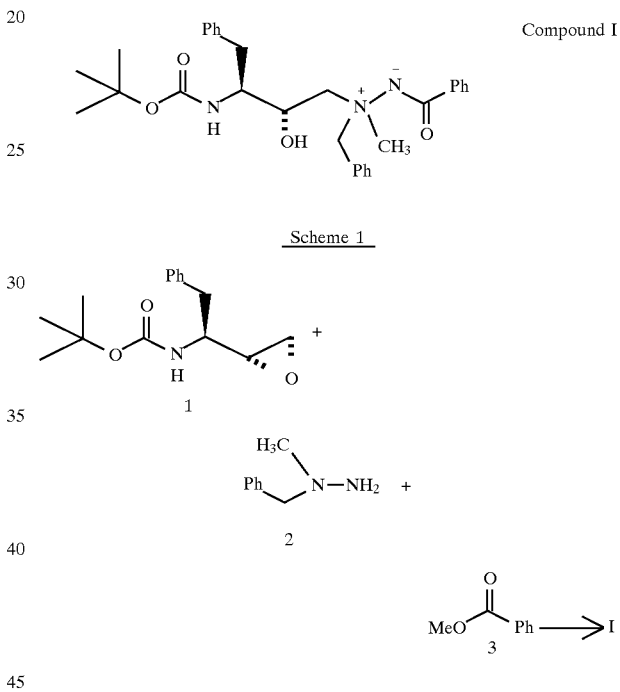

The synthesis of compound I is depicted in Scheme 1. To an isopropanol solution of 1.43 mmol of a chiral epoxide 1 (prepared using the method of Luly, et al., *J. Org. Chem.*, 1987, 52, 1487) and 1.43 mmol of hydrazine 2 (synthesized from the procedure of Ohme, R.; Preuschof, H., *J. Pract. Chem.*, 1970, 312, 349) is added 1.43 mmol of the commercially available methyl ester 3. The reaction is stirred at 60° C. for 5 h. HPLC analysis of the crude reaction indicated the presence of two diastereomers, which is expected due to the fixed chirality of the hydroxyethyl component and the resulting quaternary nitrogen of compound I. The solvent is removed under reduced pressure, and the crude oil is partially purified via silica gel column chromatography. A sample for enzymological testing is acquired by further purifying the isolated material by recrystallization to afford a white, crystalline solid product. The product is shown to be the desired compound I by $H^1$ NMR and mass spectroscopy. HPLC analysis of the product indicates that isomer (a) of compound I is obtained free of isomer (b) after column chromatography and repeated crystallization.

Experimental: Enzymology

The inhibition constant ($K_i$) of compound Ia is determined using HIV-1 protease kit supplied by NovaBiochem (cat.

10-39-0001, which supplies a solid phase synthesized analog of the protease, incorporating the unnatural residue aminobutyric acid in place of both cysteine residues 67 and 95, along with a thioester linkage in place of the normal peptide bond between residues 51–52). A fluorometric assay is performed using a fluorogenic substrate supplied by NovaBiochem (cat. #05-23-5216, Abz-Thr-Ile-Nle-Phe $(NO_2)$-Gln-Arg-$NH_2$). Initial rates of substrate hydrolysis are determined by following the increase in the fluorescence emission at 420 nm (excitation is at 325 nm) as the substrate is digested by the protease. The initial rates of substrate cleavage is determined in the absence and presence of compound Ia (up to a concentration of Ia=500 nM). A Lineweaver-Burk analysis of Ia indicates that inhibition follows classical competitive inhibition (FIG. 4). Replotting the slopes from the Lineweaver-Burk plot (FIG. 5) gives a calculated $K_i$ value of 137 nM.

Given the potency of this inhibitor for HIV-1 protease, the model of the bound complex was used to rationalize structure-activity relationships for a variety of substituents and to propose additional compounds for synthesis and evaluation. In particular, fragments from all three components of the inhibitor (the epoxide, the ester and the hydrazine) were evaluated as to the most feasible ways to maximize both hydrophobic and hydrogen bonding interactions complementary with the protein.

The scope of the following claims is intended to encompass all obvious changes in the elements, details, aterials and arrangement of parts that will occur to one of ordinary skill in the art.

We claim:

1. A method of making a first chemical compound having a complementary structure to a second chemical compound comprising the steps of preparing a first chemical compound having a chemical backbone of formula I:

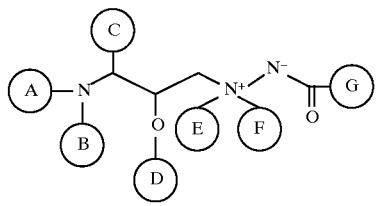

wherein A, B, C, D, E, F and G are structural diversity elements which are the same or different; and testing to determine whether the compound has complementary properties with a second chemical compound.

2. A method according to claim 1 wherein structural diversity element D is hydrogen.

3. A method according to claim 2 wherein structural diversity element B is hydrogen.

4. A method according to claim 1 wherein each of structural diversity elements A, B, E and F is hydrogen, carbonyl, alkyl, or aryl; and structural diversity element D is hydrogen, alkyl or aryl.

5. A method according to claim 1 wherein each of structural diversity elements C and G is a vinyl group, an oxirane group, an azlactone, a lactone, an acid chloride, a carboxylic acid, an ester, hydroxyl, amino, an alkyl halide or an aryl halide.

6. A method according to claim 1 wherein structural diversity element A is an alkoxyl carbonyl group, each of structural diversity elements B, D and F is hydrogen or alkyl, and each of structural diversity elements C, E and G is alkyl, aryl or carbocyclic.

7. A method according to claim 1 wherein structural diversity elements A and B or E and F are peptides, such that A and B or E and F form a heterocyclic ring structure.

8. A method according to claim 1 wherein structural diversity element D is hydrogen, a branched or straight chain alkyl group having from 1–8 carbon atoms, an ether group, and an ester group.

9. A method according to claim 1 wherein each structural diversity element is independently selected from the group consisting of hydrogen; hydroxyl; alkyl; alkoxy; alkyl halide; hydroxyalkyl; amino; amido; urea; carbanion; carboxylic; carbocyclic; aryl; carbonyl; carboxyl; ester; aldehyde; ether; azalactone; and peptide.

10. A method according to claim 1 wherein each of structural diversity elements C and G contains one of a vinyl group, an oxirane group, an azalactone, a lactone, an acid chloride, a carboxylic acid, an ester, hydroxyl, amino, an alkyl halide or an aryl halide.

11. A method according to claim 1 wherein each of structural diversity elements B, D and F is hydrogen or alkyl, and structural diversity elements A, C, E and G are present in the combinations shown in the following table:

| A | E | F | G |
|---|---|---|---|
| [tert-butyl carbamate] | [phenyl] | [benzyl] | [isopropenyl] |
| [tert-butyl carbamate] | [phenyl] | [CH₃] | [phenyl] |
| [tert-butyl carbamate] | [phenyl] | [3-aminobenzyl] | [phenyl] |

-continued
| A | E | F | G |
|---|---|---|---|
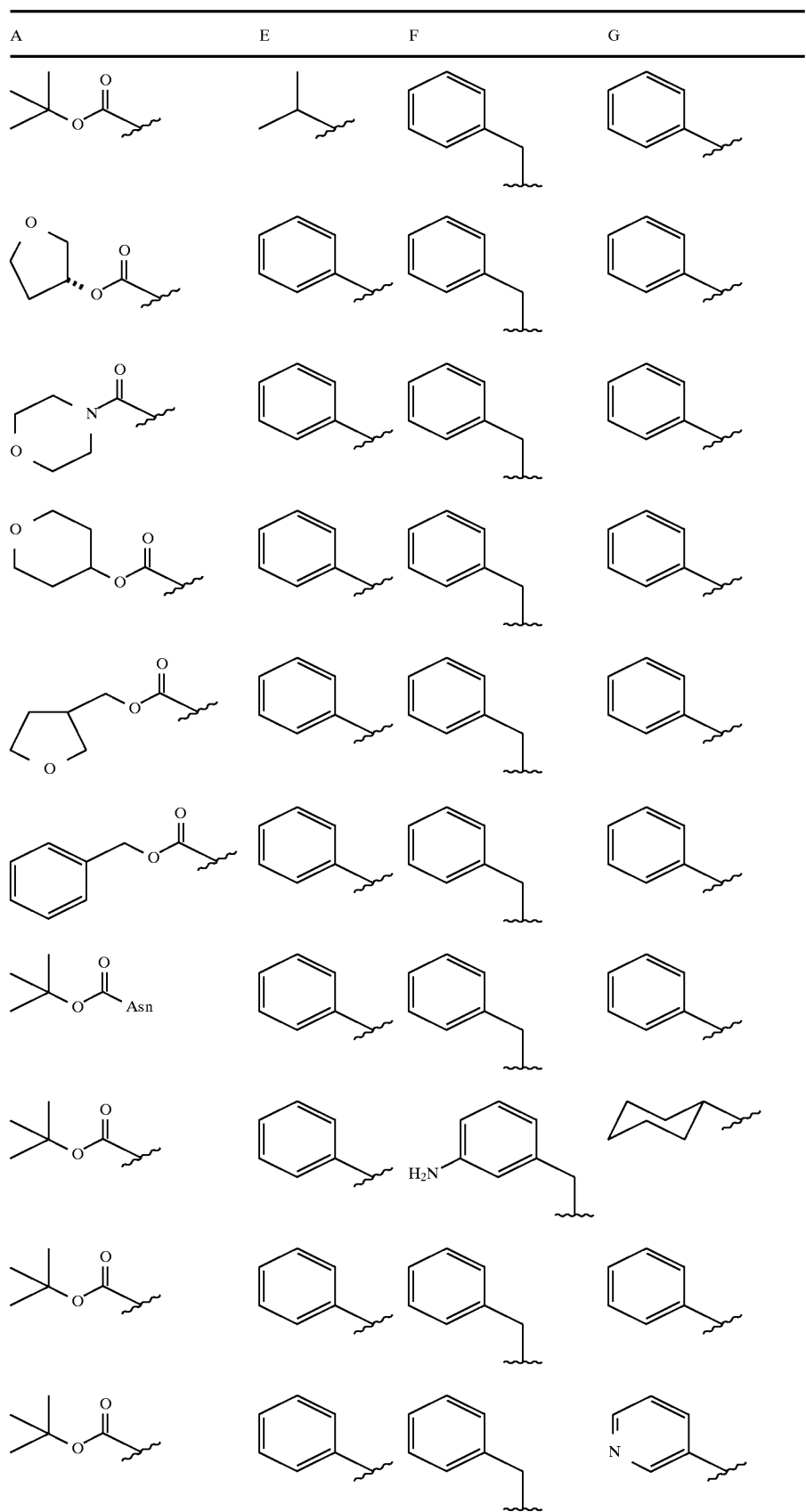

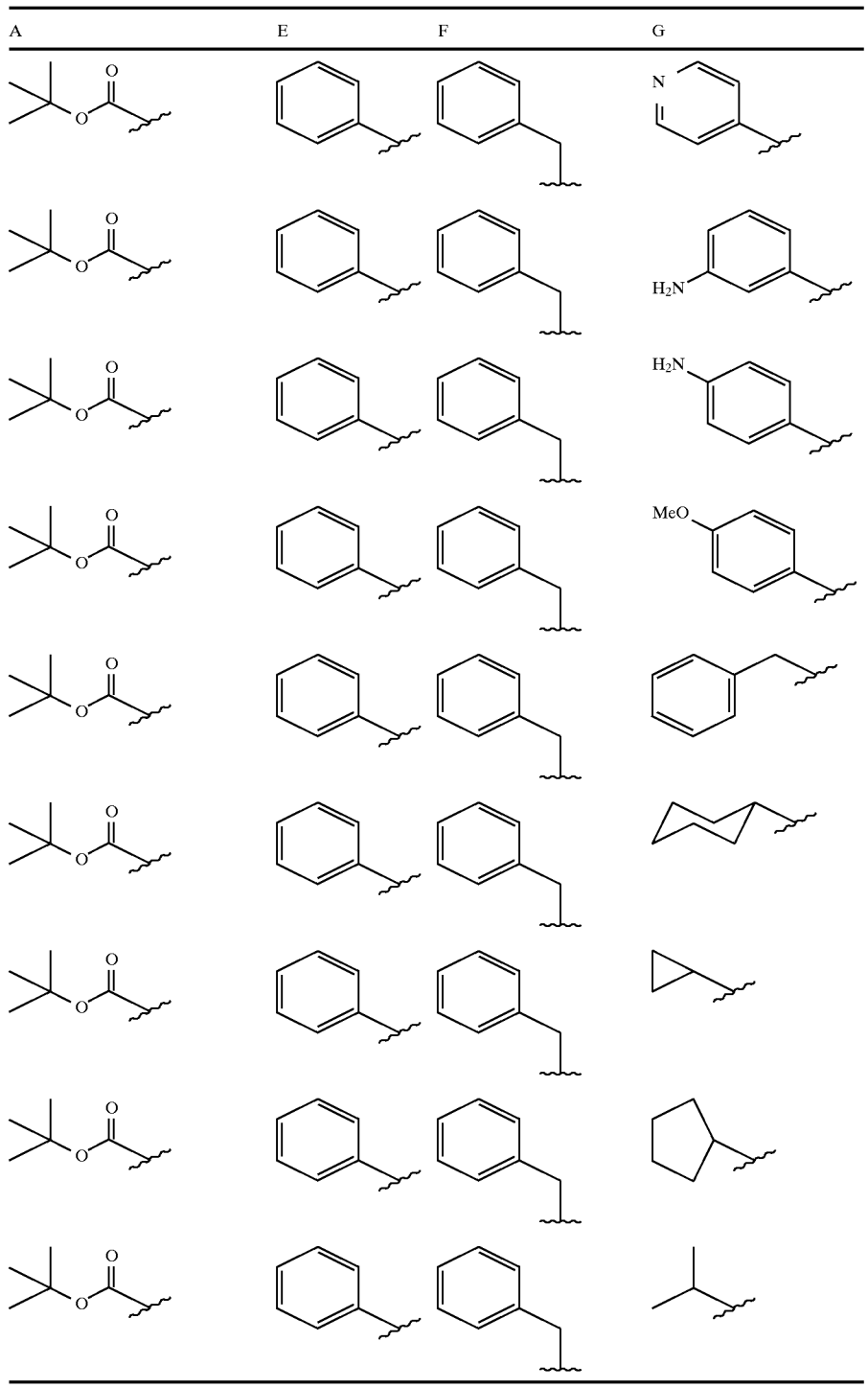

12. A method according to claim 1 wherein structural diversity element A is one of hydrogen, alkyl, alkylhalide, hydroxyalkyl, amino, amido, urea, aryl, carboxyl, or a peptide; structural diversity element B is one of amino, amido, urea, a peptide, carboxylic, aryl, carbonyl, ester, aldehyde, ether or azalactone; structural diversity element D is one of hydrogen, alkyl or aryl; structural diversity element E is one of amino, amido or a peptide; structural diversity element F is one of amino, amido or a peptide; and structural diversity element G is one of amino, urea, aryl, carbonyl, ester or azalactone.

13. A method according to claim 1 wherein structural diversity elements A, B, C, D, E, F and G are the same or different, and each is selected from the group consisting of a chemical bond; hydrogen; an electrophilic group; a nucleophilic group; an amino acid derivative; a nucleotide derivative; a carbohydrate derivative; an organic structural motif; a reporter element; an organic moiety, optionally containing a polymerizable group; or a macromolecular component.

14. A peptide isostere capable of binding to an active site of a receptor or to an enzyme, comprising a compound having a chemical backbone of formula I:

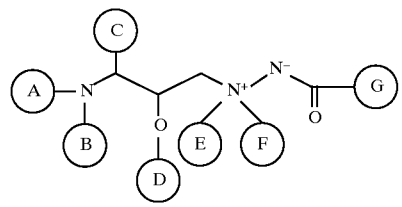

wherein A, B, C, D, E, F and G are structural diversity elements which are the same or different.

15. The peptide isostere according to claim 14, wherein structural diversity elements A, B, C, D, E, F and G are the same or different, and each is selected from the group consisting of a chemical bond; hydrogen; an electrophilic group; a nucleophilic group; an amino acid derivative; a nucleotide derivative; a carbohydrate derivative; an organic structural motif; a reporter element; an organic moiety, optionally containing a polymerizable group; or a macromolecular component.

16. The peptide isostere according to claim 14 wherein each of structural diversity elements A, B, E and F is hydrogen, carbonyl, alkyl, or aryl; and structural diversity element D is hydrogen, alkyl or aryl.

17. The peptide isostere according to claim 14 wherein each of structural diversity elements C and G is a vinyl group, an oxirane group, an azlactone, a lactone, an acid chloride, a carboxylic acid, an ester, hydroxyl, amino, an alkyl halide or an aryl halide.

18. The peptide isostere according to claim 14 wherein structural diversity element A is an alkoxyl carbonyl group, each of structural diversity elements B, D and F is hydrogen or alkyl, and each of structural diversity elements C, E and G is alkyl, aryl or carbocyclic.

19. The peptide isostere according to claim 14 wherein structural diversity elements A and B or E and F are peptides, such that A and B or E and F form a heterocyclic ring structure.

20. The peptide isostere according to claim 14 wherein structural diversity element D is hydrogen, a branched or straight chain alkyl group having from 1–8 carbon atoms, an ether group, and an ester group.

21. The peptide isostere according to claim 14 wherein each structural diversity element is independently selected from the group consisting of hydrogen; hydroxyl; alkyl; alkoxy; alkyl halide; hydroxyalkyl; amino; amido; urea; carbanion; carboxylic; carbocyclic; aryl; carbonyl; carboxyl; ester; aldehyde; ether; azalactone; and peptide.

22. The peptide isostere according to claim 14 wherein each of structural diversity elements C and G contains one of a vinyl group, an oxirane group, an azalactone, a lactone, an acid chloride, a carboxylic acid, an ester, hydroxyl, amino, an alkyl halide or an aryl halide.

23. A peptide isostere capable of binding to an active site of a receptor or to an enzyme, wherein each of structural diversity elements B, D and F is hydrogen or alkyl, and structural diversity elements A, C, E and G are present in the combinations shown in the following table:

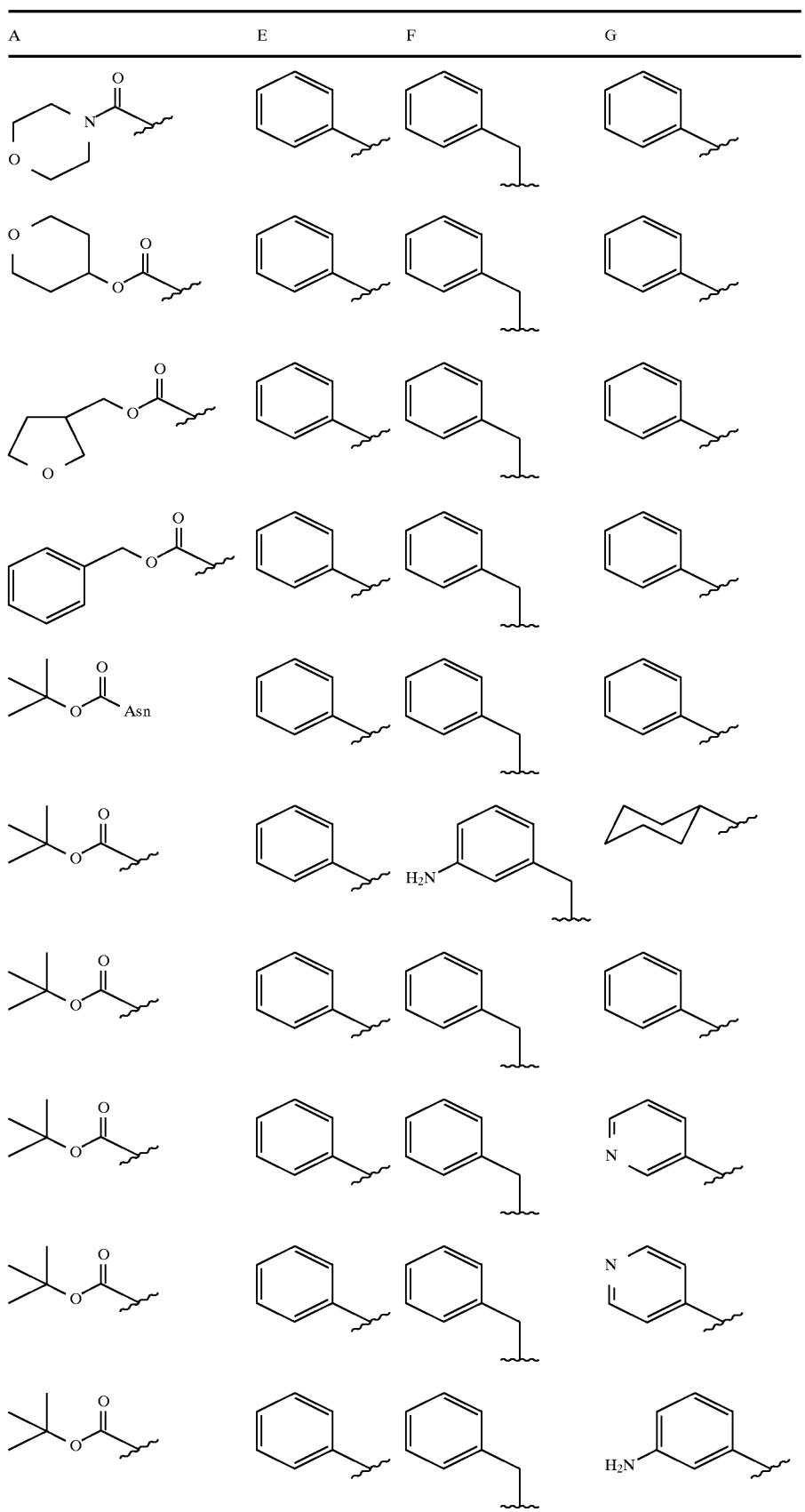

-continued
| A | E | F | G |
|---|---|---|---|
| | | | |
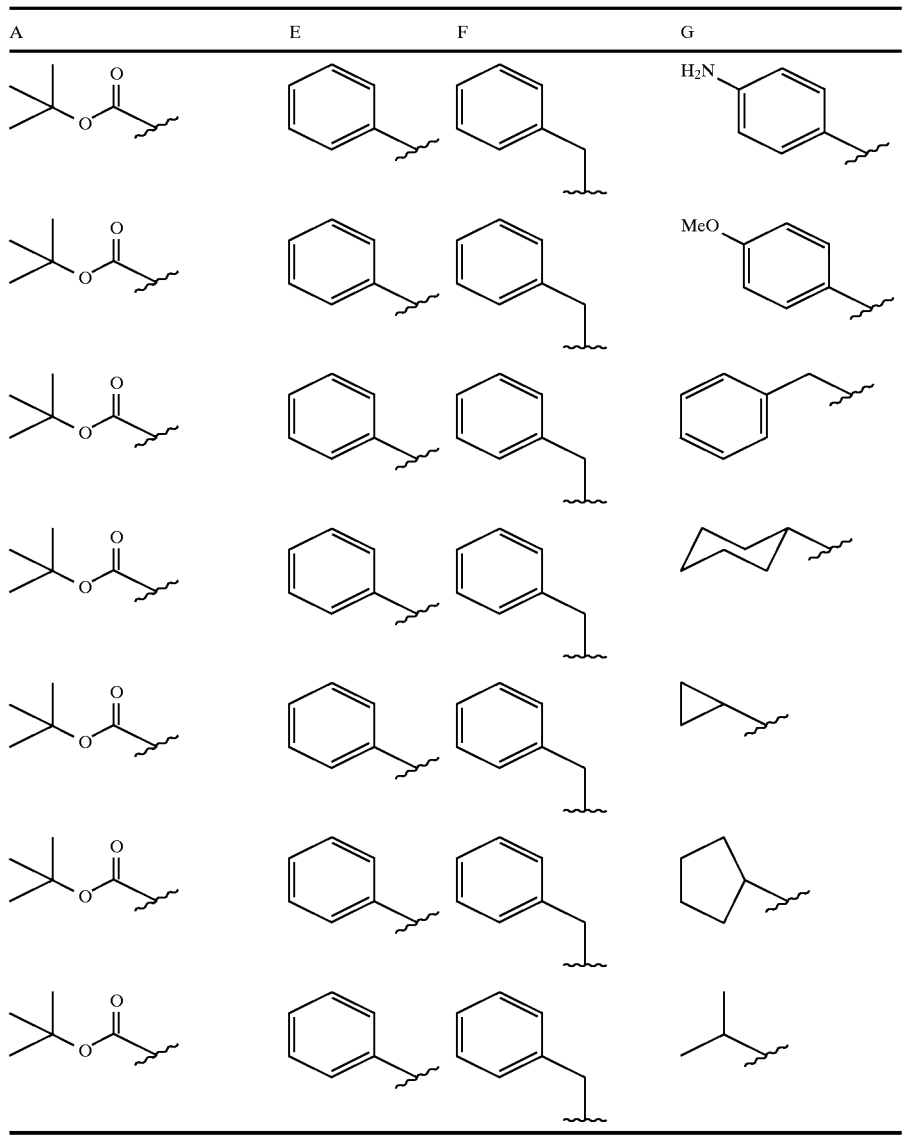
* * * * *